(12) United States Patent
Stein et al.

(10) Patent No.: US 9,161,717 B2
(45) Date of Patent: Oct. 20, 2015

(54) ORTHOPEDIC INSERT MEASURING SYSTEM HAVING A SEALED CAVITY

(75) Inventors: Marc Stein, Chandler, AZ (US);
Andrew P. Miller, Gilbert, AZ (US);
Andrew U. Chase, Chandler, AZ (US);
Jason Addink, Gilbert, AZ (US)

(73) Assignee: ORTHOSENSOR INC., Dania Beach, FL (US)

( * ) Notice: Subject to any disclaimer, the term of this patent is extended or adjusted under 35 U.S.C. 154(b) by 882 days.

(21) Appl. No.: 13/244,227

(22) Filed: Sep. 23, 2011

(65) Prior Publication Data
US 2013/0079674 A1 Mar. 28, 2013

(51) Int. Cl.
| A61B 17/60 | (2006.01) |
|---|---|
| A61F 2/00 | (2006.01) |
| A61B 5/00 | (2006.01) |
| A61F 2/46 | (2006.01) |
| A61B 5/11 | (2006.01) |
| A61F 2/38 | (2006.01) |

(52) U.S. Cl.
CPC ............... *A61B 5/4585* (2013.01); *A61B 5/686* (2013.01); *A61F 2/4657* (2013.01); *A61B 5/0031* (2013.01); *A61B 5/11* (2013.01); *A61B 5/6882* (2013.01); *A61B 2560/0406* (2013.01); *A61B 2562/24* (2013.01); *A61F 2/4684* (2013.01); *A61F 2002/3895* (2013.01); *A61F 2002/4666* (2013.01)

(58) Field of Classification Search
CPC ............................ A61B 5/4585; A61B 5/4851
USPC .......... 600/587, 594, 595; 606/88; 623/17.15, 623/18.11, 20.14–20.36; 73/781, 862.041
See application file for complete search history.

(56) References Cited

U.S. PATENT DOCUMENTS

| 3,727,616 | A | 4/1973 | Lenzkes |
|---|---|---|---|
| 4,066,082 | A | 1/1978 | Arcan et al. |
| 4,092,597 | A | 5/1978 | Place |
| 4,127,110 | A | 11/1978 | Bullara |
| 4,277,758 | A | 7/1981 | Mishiro |
| 4,480,485 | A | 11/1984 | Bradshaw et al. |

(Continued)

FOREIGN PATENT DOCUMENTS

| CN | 101254103 | 9/2006 |
|---|---|---|
| CN | 101426453 | 5/2009 |

(Continued)

OTHER PUBLICATIONS

International Search Report for PCT/US2012/056689 dated Feb. 25, 2013, 4 pages.

(Continued)

*Primary Examiner* — Brian Szmal

(57) ABSTRACT

At least one embodiment is directed to an insert for measuring a parameter of the muscular-skeletal system. The insert can be temporary or permanent. In one embodiment, the insert is prosthetic component for a single compartment of the knee. The insert comprises a support structure and a support structure respectively having an articular surface and a load bearing surface. The height of the insert is less than 10 millimeters. At least one internal cavity is formed when support structures are coupled together for housing electronic circuitry, sensors, and the power source. The internal cavity is isolated from the external environment and can be hermetically sealed. The exterior surfaces of the support structure and the support structure are sterilized.

16 Claims, 12 Drawing Sheets

(56) References Cited

U.S. PATENT DOCUMENTS

| | | |
|---|---|---|
| 4,524,766 A | 6/1985 | Petersen |
| 4,731,762 A | 3/1988 | Hanks |
| 4,764,804 A | 8/1988 | Sahara et al. |
| 4,857,893 A | 8/1989 | Carrol |
| 4,864,463 A | 9/1989 | Shkedi et al. |
| 4,899,761 A | 2/1990 | Brown et al. |
| 4,902,958 A | 2/1990 | Cook, II |
| 4,920,279 A | 4/1990 | Charlet et al. |
| 4,983,533 A | 1/1991 | Go |
| 4,986,281 A | 1/1991 | Preves et al. |
| 5,042,489 A | 8/1991 | Wiener et al. |
| 5,119,676 A | 6/1992 | Bower et al. |
| 5,456,724 A | 10/1995 | Yen et al. |
| 5,470,354 A | 11/1995 | Hershberger et al. |
| 5,569,260 A | 10/1996 | Petersen |
| 5,650,571 A | 7/1997 | Freud et al. |
| 5,669,914 A | 9/1997 | Eckhoff |
| 5,683,396 A | 11/1997 | Tokish et al. |
| 5,688,279 A | 11/1997 | McNulty et al. |
| 5,733,292 A | 3/1998 | Gustilo et al. |
| 5,871,018 A | 2/1999 | Delp et al. |
| 5,900,592 A | 5/1999 | Sohns et al. |
| 6,070,469 A | 6/2000 | Taniguchi et al. |
| 6,072,784 A | 6/2000 | Agrawal et al. |
| 6,115,636 A | 9/2000 | Ryan |
| 6,165,142 A | 12/2000 | Bar |
| 6,245,109 B1 | 6/2001 | Mendes et al. |
| 6,425,920 B1 | 7/2002 | Hamada |
| 6,429,585 B1 | 8/2002 | Kitazume et al. |
| 6,443,891 B1 | 9/2002 | Grevious |
| 6,447,448 B1 | 9/2002 | Ishikawa et al. |
| 6,583,630 B2 | 6/2003 | Mendes et al. |
| 6,621,278 B2 | 9/2003 | Ariav |
| 6,739,068 B1 | 5/2004 | Rinner |
| 6,796,988 B2 | 9/2004 | Melkent et al. |
| 6,856,141 B2 | 2/2005 | Ariav |
| 6,859,661 B2 | 2/2005 | Tuke |
| 6,993,393 B2 | 1/2006 | Von Arx et al. |
| 7,035,077 B2 | 4/2006 | Brendel |
| 7,080,554 B2 | 7/2006 | Ariav et al. |
| 7,097,662 B2 | 8/2006 | Evans, III et al. |
| 7,141,020 B2 | 11/2006 | Poland et al. |
| 7,153,281 B2 | 12/2006 | Holmes |
| 7,173,749 B2 | 2/2007 | Maleki et al. |
| 7,179,295 B2 * | 2/2007 | Kovacevic ................. 623/17.15 |
| 7,195,645 B2 | 3/2007 | Disilvestro et al. |
| 7,195,654 B2 | 3/2007 | Jackson et al. |
| 7,215,599 B2 | 5/2007 | Nishimori et al. |
| 7,256,695 B2 * | 8/2007 | Hamel et al. ............... 340/572.1 |
| 7,266,989 B2 | 9/2007 | Ariav |
| 7,283,867 B2 | 10/2007 | Strother et al. |
| 7,344,493 B2 | 3/2008 | Sonnenschein et al. |
| 7,347,817 B2 | 3/2008 | Glukhovsky et al. |
| 7,378,916 B2 | 5/2008 | Oita et al. |
| 7,384,403 B2 | 6/2008 | Sherman |
| 7,396,336 B2 | 7/2008 | Orszulak et al. |
| 7,412,897 B2 | 8/2008 | Crottet et al. |
| 7,442,196 B2 | 10/2008 | Fisher et al. |
| 7,454,972 B2 | 11/2008 | Heyman et al. |
| 7,477,926 B2 | 1/2009 | McCombs |
| 7,519,422 B2 | 4/2009 | Lippert et al. |
| 7,559,951 B2 | 7/2009 | DiSilvestro et al. |
| 7,575,602 B2 | 8/2009 | Amirouche et al. |
| 7,578,821 B2 | 8/2009 | Fisher et al. |
| 7,615,055 B2 | 11/2009 | DiSilvestro |
| 7,630,774 B2 | 12/2009 | Karni et al. |
| 7,632,283 B2 | 12/2009 | Heldreth |
| 7,643,862 B2 | 1/2010 | Schoenefeld |
| 7,668,201 B2 | 2/2010 | Sharony et al. |
| 7,725,288 B2 | 5/2010 | Boillot |
| 7,769,947 B2 | 8/2010 | Ranganathan et al. |
| 7,819,826 B2 | 10/2010 | Diederich et al. |
| 7,918,887 B2 | 4/2011 | Roche |
| 8,000,926 B2 | 8/2011 | Roche |
| 8,070,695 B2 | 12/2011 | Gupta et al. |
| 8,098,544 B2 | 1/2012 | Roche |
| 8,099,168 B2 | 1/2012 | Roche |
| 8,141,437 B2 | 3/2012 | Amirouche et al. |
| 8,167,823 B2 | 5/2012 | Nycz et al. |
| 8,169,185 B2 | 5/2012 | Partovi et al. |
| 8,197,549 B2 | 6/2012 | Amirouche et al. |
| 8,211,041 B2 | 7/2012 | Fisher et al. |
| 8,245,583 B2 * | 8/2012 | Stein .................. 73/862.636 |
| 8,270,253 B1 | 9/2012 | Roche et al. |
| 8,295,920 B2 | 10/2012 | Bouton et al. |
| 8,372,147 B2 | 2/2013 | Roche |
| 8,372,153 B2 | 2/2013 | Roche |
| 8,421,642 B1 | 4/2013 | Mcintosh et al. |
| 8,444,654 B2 | 5/2013 | Roche |
| 8,449,556 B2 | 5/2013 | Roche |
| 8,494,805 B2 | 7/2013 | Roche et al. |
| 8,498,711 B2 | 7/2013 | Roche |
| 8,689,647 B2 * | 4/2014 | Stein .................. 73/862.636 |
| 2002/0029784 A1 | 3/2002 | Stark |
| 2002/0049394 A1 | 4/2002 | Roy et al. |
| 2002/0087075 A1 | 7/2002 | Bucholz |
| 2003/0004518 A1 | 1/2003 | Perren et al. |
| 2003/0036713 A1 | 2/2003 | Bouton et al. |
| 2003/0036764 A1 | 2/2003 | Hamada |
| 2003/0069644 A1 | 4/2003 | Kovacevic et al. |
| 2003/0114898 A1 | 6/2003 | Von Arx et al. |
| 2003/0187351 A1 | 10/2003 | Franck et al. |
| 2003/0187452 A1 | 10/2003 | Smith et al. |
| 2004/0011365 A1 | 1/2004 | Govari et al. |
| 2004/0064073 A1 * | 4/2004 | Heldreth ................. 600/595 |
| 2004/0131013 A1 | 7/2004 | Ise et al. |
| 2004/0152970 A1 | 8/2004 | Hunter et al. |
| 2004/0184351 A1 | 9/2004 | Nishimori et al. |
| 2004/0215079 A1 | 10/2004 | Omura et al. |
| 2005/0010299 A1 | 1/2005 | Disilvestro |
| 2005/0010302 A1 | 1/2005 | Dietz et al. |
| 2005/0020941 A1 | 1/2005 | Tarabichi |
| 2005/0234555 A1 | 10/2005 | Sutton |
| 2005/0252294 A1 | 11/2005 | Ariav |
| 2005/0267485 A1 | 12/2005 | Cordes et al. |
| 2005/0273170 A1 | 12/2005 | Navarro et al. |
| 2006/0058798 A1 | 3/2006 | Roman et al. |
| 2006/0069436 A1 | 3/2006 | Sutton et al. |
| 2006/0132120 A1 | 6/2006 | Luber et al. |
| 2006/0161051 A1 | 7/2006 | Terrill-Grisoni et al. |
| 2006/0184067 A1 | 8/2006 | Clark et al. |
| 2006/0195042 A1 | 8/2006 | Flaherty |
| 2006/0206014 A1 | 9/2006 | Ariav |
| 2006/0232408 A1 | 10/2006 | Nycz |
| 2006/0241422 A1 | 10/2006 | Muratayev et al. |
| 2006/0241569 A1 | 10/2006 | DiSilvestro |
| 2006/0271112 A1 | 11/2006 | Martinson |
| 2007/0129776 A1 | 6/2007 | Robins et al. |
| 2007/0219561 A1 | 9/2007 | Lavallee et al. |
| 2007/0233065 A1 | 10/2007 | Donofrio et al. |
| 2007/0233267 A1 | 10/2007 | Amirouche et al. |
| 2007/0234819 A1 * | 10/2007 | Amirouche et al. ............ 73/781 |
| 2007/0239165 A1 | 10/2007 | Amirouche |
| 2007/0242652 A1 | 10/2007 | Dahlman et al. |
| 2007/0258674 A1 | 11/2007 | Wang |
| 2007/0272747 A1 | 11/2007 | Woods et al. |
| 2007/0282451 A1 | 12/2007 | Metzger et al. |
| 2008/0082118 A1 | 4/2008 | Edidin et al. |
| 2008/0129486 A1 | 6/2008 | Jeckelmann et al. |
| 2008/0133016 A1 | 6/2008 | Heinz |
| 2008/0191584 A1 | 8/2008 | Malkin |
| 2008/0228195 A1 | 9/2008 | Von Jako et al. |
| 2008/0228231 A1 | 9/2008 | Raphael et al. |
| 2009/0112207 A1 | 4/2009 | Walker et al. |
| 2009/0167719 A1 | 7/2009 | Woolley |
| 2009/0264894 A1 | 10/2009 | Wasielewski |
| 2010/0010494 A1 | 1/2010 | Quirno |
| 2010/0022874 A1 | 1/2010 | Wang et al. |
| 2010/0076505 A1 | 3/2010 | Borja |
| 2010/0076563 A1 | 3/2010 | Otto et al. |
| 2010/0100010 A1 | 4/2010 | Andarawis et al. |
| 2010/0100130 A1 | 4/2010 | Carl et al. |
| 2010/0151946 A1 | 6/2010 | Wilson et al. |
| 2010/0191153 A1 | 7/2010 | Sanders et al. |

(56) References Cited

U.S. PATENT DOCUMENTS

| | | |
|---|---|---|
| 2010/0198067 A1 | 8/2010 | Mahfouz et al. |
| 2010/0198275 A1 | 8/2010 | Chana et al. |
| 2010/0204575 A1 | 8/2010 | Roche |
| 2010/0204955 A1 | 8/2010 | Roche |
| 2010/0249665 A1 | 9/2010 | Roche |
| 2010/0249787 A1 | 9/2010 | Roche |
| 2010/0249788 A1 | 9/2010 | Roche |
| 2010/0249790 A1 | 9/2010 | Roche |
| 2010/0249791 A1 | 9/2010 | Roche |
| 2010/0320973 A1 | 12/2010 | Nishida |
| 2010/0326211 A1* | 12/2010 | Stein .................. 73/862.636 |
| 2010/0328098 A1* | 12/2010 | Stein et al. ............ 340/870.3 |
| 2010/0331633 A1 | 12/2010 | Stein |
| 2010/0331683 A1* | 12/2010 | Stein et al. ............... 600/437 |
| 2010/0331734 A1* | 12/2010 | Stein ........................ 600/587 |
| 2010/0331737 A1 | 12/2010 | Stein et al. |
| 2010/0331738 A1* | 12/2010 | Stein et al. ............... 600/587 |
| 2011/0004076 A1 | 1/2011 | Janna |
| 2011/0029913 A1 | 2/2011 | Boillot |
| 2011/0032184 A1 | 2/2011 | Roche |
| 2011/0060220 A1 | 3/2011 | Roche |
| 2011/0092972 A1 | 4/2011 | Allen |
| 2011/0102455 A1 | 5/2011 | Temple |
| 2011/0160572 A1 | 6/2011 | McIntosh et al. |
| 2011/0160616 A1* | 6/2011 | Stein et al. ............... 600/587 |
| 2011/0160738 A1 | 6/2011 | McIntosh et al. |
| 2011/0257491 A1 | 10/2011 | Robertson et al. |
| 2011/0275957 A1 | 11/2011 | Bhandari |
| 2012/0016362 A1 | 1/2012 | Heinrich et al. |
| 2012/0035868 A1 | 2/2012 | Roche et al. |
| 2012/0157887 A1 | 6/2012 | Fanson |
| 2012/0209117 A1 | 8/2012 | Roche |
| 2012/0277752 A1 | 11/2012 | Wasielewski |
| 2012/0283600 A1* | 11/2012 | Stein ........................ 600/587 |
| 2013/0225982 A1 | 8/2013 | Roche |

FOREIGN PATENT DOCUMENTS

| | | |
|---|---|---|
| EP | 1800097 B1 | 5/2008 |
| WO | 2006098759 A1 | 9/2006 |
| WO | 2008120215 | 10/2008 |
| WO | 2008120215 A2 | 10/2008 |

OTHER PUBLICATIONS

International Search Report for PCT/US2012/056743 dated Mar. 27, 2013, 4 pages.

International Search Report for PCT/US2012/056702 dated Feb. 27, 2013, 7 pages.

International Search Report for PCT/US2012/056758 dated Mar. 28, 2013, 5 pages.

International Search Report for PCT/US2012/056748 dated Mar. 27, 2013, 4 pages.

International Search Report for PCT/US2012/056740 dated Feb. 26, 2013, 4 pages.

International Search Report and Written Opinion for PCT/US2014055521 dated Dec. 19, 2014.

E. Lou et al., Wireless Surgical Tools for Mechanical Measurements during Scoliosis Surgery; Proceedings of the 2005 IEEE, Engineering in Medicine and Biology 27th Annual Conference, Shanghai, China Sep. 1-4, 2005, pp. 7131-7134 (Sep. 2005).

* cited by examiner

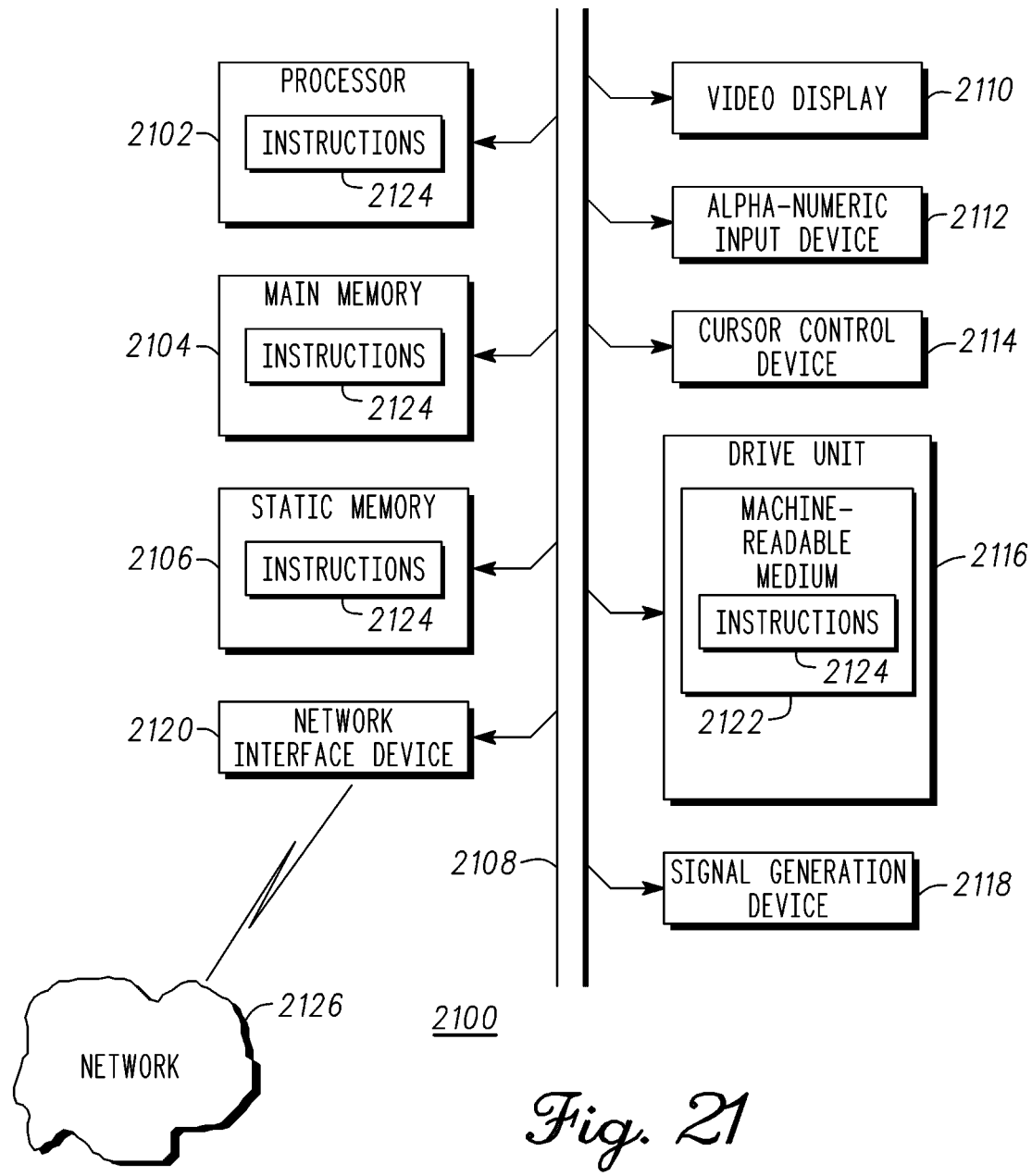

ORTHOPEDIC INSERT MEASURING SYSTEM HAVING A SEALED CAVITY

FIELD

The present invention pertains generally to a joint prosthesis, and particularly to methods and devices for assessing and determining proper loading of an implant component or components during joint reconstructive surgery and long-term monitoring of the muscular-skeletal system.

BACKGROUND

The skeletal system of a mammal is subject to variations among species. Further changes can occur due to environmental factors, degradation through use, and aging. An orthopedic joint of the skeletal system typically comprises two or more bones that move in relation to one another. Movement is enabled by muscle tissue and tendons attached to the skeletal system of the joint. Ligaments hold and stabilize the one or more joint bones positionally. Cartilage is a wear surface that prevents bone-to-bone contact, distributes load, and lowers friction.

There has been substantial growth in the repair of the human skeletal system. In general, prosthetic orthopedic joints have evolved using information from simulations, mechanical prototypes, and patient data that is collected and used to initiate improved designs. Similarly, the tools being used for orthopedic surgery have been refined over the years but have not changed substantially. Thus, the basic procedure for replacement of an orthopedic joint has been standardized to meet the general needs of a wide distribution of the population. Although the tools, procedure, and artificial joint meet a general need, each replacement procedure is subject to significant variation from patient to patient. The correction of these individual variations relies on the skill of the surgeon to adapt and fit the replacement joint using the available tools to the specific circumstance.

BRIEF DESCRIPTION OF THE DRAWINGS

Various features of the system are set forth with particularity in the appended claims. The embodiments herein, can be understood by reference to the following description, taken in conjunction with the accompanying drawings, in which:

FIG. 8 illustrates the assembled insert in accordance with an example embodiment;

FIG. 21 illustrates a diagrammatic representation of a machine in the form of a computer system within which a set of instructions, when executed, may cause the machine to perform any one or more of the methodologies discussed above.

DETAILED DESCRIPTION

Figure 1:
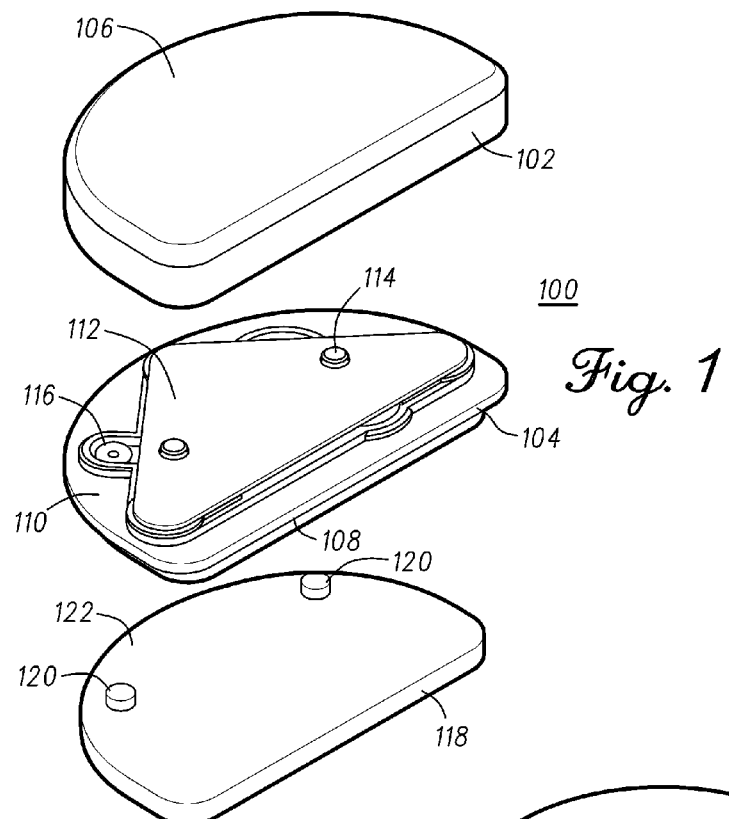
FIG. 1 illustrates an insert for measuring a parameter of the muscular-skeletal system in accordance with an example embodiment.

Embodiments of the invention are broadly directed to measurement of physical parameters. More specifically, an electro-mechanical system is directed towards the measurement of parameters related to the muscular-skeletal system. Many physical parameters of interest within physical systems or bodies are currently not measured due to size, cost, time, or measurement precision. For example, joint implants such as knee, hip, spine, shoulder, and ankle implants would benefit substantially from in-situ measurements taken during surgery to aid the surgeon in fine-tuning the prosthetic system. Measurements can supplement the subjective feedback of the surgeon to ensure optimal installation. Permanent sensors in the final prosthetic components can provide periodic data related to the status of the implant in use. Data collected intra-operatively and long term can be used to determine parameter ranges for surgical installation and to improve future prosthetic components.

The physical parameter or parameters of interest can include, but are not limited to, measurement of load, force, pressure, displacement, density, viscosity, pH, acceleration, and localized temperature. Often, a measured parameter is used in conjunction with another measured parameter to make a qualitative assessment. In joint reconstruction, portions of the muscular-skeletal system are prepared to receive prosthetic components. Preparation includes bone cuts or bone shaping to mate with one or more prosthesis. Parameters can be evaluated relative to orientation, alignment, direction, or position as well as movement, rotation, or acceleration along an axis or combination of axes by wireless sensing modules or devices positioned on or within a body, instrument, appliance, vehicle, equipment, or other physical system.

In all of the examples illustrated and discussed herein, any specific materials, such as temperatures, times, energies, and material properties for process steps or specific structure implementations should be interpreted to be illustrative only and non-limiting. Processes, techniques, apparatus, and materials as known by one of ordinary skill in the art may not be discussed in detail but are intended to be part of an enabling description where appropriate. It should also be noted that the word "coupled" used herein implies that elements may be directly coupled together or may be coupled through one or more intervening elements.

Note that similar reference numerals and letters refer to similar items in the following figures. In some cases, numbers from prior illustrations will not be placed on subsequent figures for purposes of clarity. In general, it should be assumed that structures not identified in a figure are the same as previous prior figures.

In the present invention parameters are measured with an integrated wireless sensing module or device comprising an i) encapsulating structure that supports sensors and contacting surfaces and ii) an electronic assemblage that integrates a power supply, sensing elements, an accelerometer, antennas and electronic circuitry that processes measurement data as well as controls all operations of energy conversion, propagation, and detection and wireless communications. The wireless sensing module or device can be positioned on or within, or engaged with, or attached or affixed to or within, a wide range of physical systems including, but not limited to instruments, appliances, vehicles, equipments, or other physical systems as well as animal and human bodies, for sensing and communicating parameters of interest in real time.

FIG. 1 is an illustration of an insert 100 for measuring a parameter of the muscular-skeletal system in accordance with an example embodiment. In general, insert 100 is a self-contained measurement system that includes an internal power source such as a battery or an inductively charged capacitor. In at least one embodiment, the system is a low cost system that can be disposed of after use in a single intra-operative procedure. In the disposable embodiment, insert 100 cannot be re-sterilized nor can the power source be replaced without comprising device integrity. Thus, operation is limited to a single use. In the intra-operative environment, insert 100 is disposed of similar to other materials or components exposed to biological matter. Alternatively, insert 100 can be a permanent implantable device or designed for a sterilization process that allows re-use.

In the intra-operative example, insert 100 is a component of a joint replacement system that facilitates movement of the muscular-skeletal system. In the illustration, the prosthetic insert 100 has a single articular surface 106 and a load-bearing surface 108 for supporting compressive loads applied by the muscular-skeletal system in more than one position. Insert 100 comprises a support structure 102 and a support structure 104 that form a housing or enclosure for the measurement system. Support structures 102 and 104 when coupled have one or more cavities therein that are isolated from an external environment. Support structures 102 and 104 respectively have articular surface 106 and load-bearing surface 108. The load-bearing surface 108 can be shaped to couple with a prosthetic component. The height or thickness of insert 100 can be adjusted by selection and attachment of a shim 118 that is coupled to load-bearing surface 106. In one embodiment, load-bearing surface 108 does not interface with a tibial prosthetic component. Shim 118 can be also required as part of insert 100 assembly. Shim 118 can be designed to align with and be retained for a specific tibial prosthetic component. This is beneficial in providing flexibility in supporting many different types of prosthetic component families with a single measurement system. Shim 118 is a passive low cost component that can be provided in many shapes and sizes. Alternatively, support structure 104 can be shaped for a specific tibial prosthetic component such that insert 100 can only be mated to the tibial prosthetic component or a family of prosthetic components. The shim 118 includes features 120 extending from a surface 122. In the example, the features 120 are cylindrical columns. The cylindrical columns are inserted into corresponding openings in the load-bearing surface 108 of support structure 104. An interference or clearance fit provides sufficient retention to hold shim 118 to support structure 104 while allowing removal from insert 100 thereafter for shim replacement. The shim 118 provides a surface substantially equal to the load-bearing surface 108 for being received and retained by a tibial prosthetic component. Although a single shim 118 is shown, the system will provide multiple shims of varying height that can be used for height adjustment.

Typically, a joint replacement includes one or more prosthetic components that are coupled to surgically prepared bone surfaces. One prosthetic component has a surface that interfaces with the articular surface 106 of the insert 100 allowing movement of the joint. As mentioned previously, load-bearing surface 108 can interface with a prosthetic component attached to a prepared bone surface. The load-bearing surface 108 typically does not support movement and has a much larger surface area supporting the compressive loading applied by the muscular-skeletal system. The articular surface 106 is low friction and can absorb loading that occurs naturally based on situation or position. In one embodiment, the articular surface 106 flexes under loading as will be disclosed in more detail below. The contact area between surfaces of the insert 100 and the prosthetic component can vary over the range of motion and the loading on the joint. Ligaments, muscle, and tendons hold the joint together and motivate the joint throughout the range of motion. In a permanent implant example, articular surface 106 of the insert 100 will wear over time due to friction produced by the prosthetic component surface contacting the articular surface 106 during movement of the joint.

Insert 100 is an active device providing measurement capability having a power source, electronic circuitry, and sensors within the body of the prosthetic component. A printed circuit board is used as a mounting substrate and to couple the electronic components to form the measurement system. Flexible interconnect is used to couple the sensors to the electronic circuitry. The flexible interconnect will be discussed in more detail hereinbelow. In the example, insert 100 is used intra-operatively to measure parameters of the muscular-skeletal system to aid in the installation of one or more prosthetic components. Operation of insert 100 is shown as a uni-condylar knee insert to illustrate operation and measurement of one or more parameters such as loading and load position. Insert 100 can be adapted for use in other prosthetic joints having articular surfaces such as the hip, spine, shoulder, and ankle. Insert 100 can also be used in a static environment within the muscular-skeletal system.

In both intra-operative and permanent embodiments, insert 100 is substantially equal in dimensions to a passive final prosthetic insert. In general, the substantially equal dimensions correspond to size and shape that allow insert 100 to fit substantially equal to the passive final prosthetic insert within the joint. In the intra-operative example, the measured loading and position of loading using insert 100 as a trial insert would be substantially equal to the loading seen by the final insert having equal heights. It should be noted that insert 100 for intra-operative measurement can be dissimilar in shape or have missing features that do not benefit the trial during operation. Insert 100 is positionally stable throughout the range of motion similar to the final insert. In the example, the exterior structure of insert 100 is formed from support structures 102 and 104 coupled together. Support structures 102 and 104 have interior surfaces that couple together to isolate an interior cavity of insert 100 from an external environment. The interior surface 110 of support structure 104 interfaces with a corresponding interior surface of support structure 102. Surface 110 is a peripheral interior surface of support structure 104. The coupling of interior surfaces of support structures 102 and 104 can be permanent or temporary. For example, support structures 102 and 104 can be fastened by slot and tab for a temporary connection or welded/glued for a permanent connection. Support structures 102 and 104 have major surfaces that are loaded by the muscular-skeletal system. Insert 100 is shown as a uni-condylar knee insert to illustrate general concepts but is not limited to this configuration. Accelerated wear of the articular surface of the final insert can occur if the contact area is insufficient to support the load. Similarly, accelerated wear can occur if the contact location is not optimal to the insert. The contact position can also vary depending on the position of the muscular-skeletal system. Insert 100 measures the load and position of load applied by the muscular-skeletal system to the articular surface. The measurements are used to aid the surgeon in selection of the final insert and in making adjustments such that the loading and position of load fall within a predetermined range found to optimize performance and wear of the joint system. The surgeon can use techniques such as soft tissue tensioning or bone modification with insert 100 in place to adjust the load magnitude and position of the applied load using real-time feedback from the sensing system to track the result of each correction.

Figure 2:
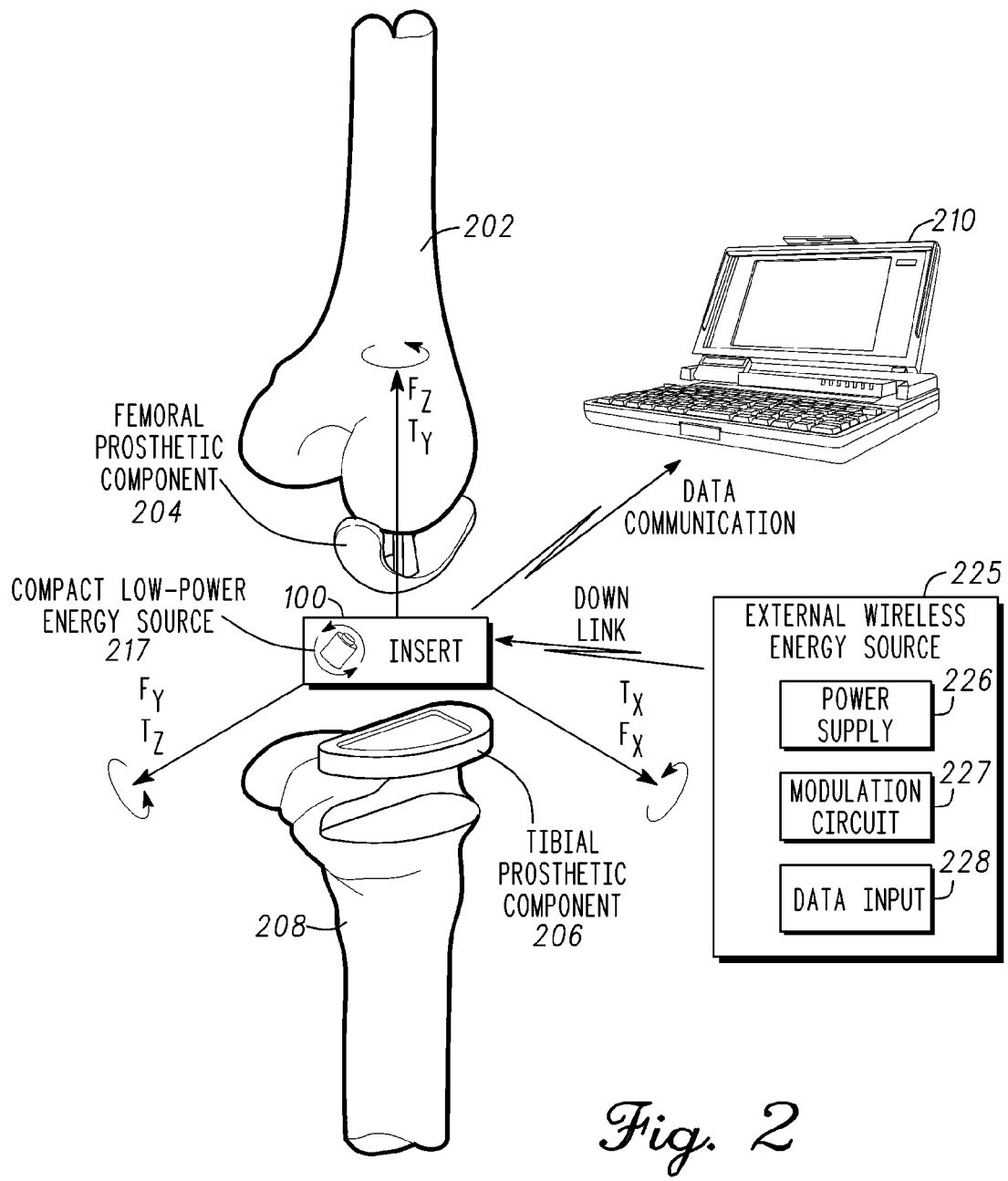
FIG. 2 illustrates an application of the insert sensing device in accordance with an example embodiment.

FIG. 2 illustrates an application of insert sensing device 100 in accordance with an example embodiment. Insert sensing device 100 can also be referred to as insert 100. In general, one or more natural components of the muscular-skeletal system are replaced when joint functionality substantially reduces a patient quality of life. A joint replacement is a common procedure in later life because of wear, damage, or pain to the muscular-skeletal system. Joint reconstruction can reduce pain while increasing patient mobility thereby allowing a return to normal activity. In the example, insert 100 can intra-operatively assess a load on the prosthetic knee components and collect load data for real-time viewing of the load over various angles of flexion. By way of an integrated antenna, a compact low-power energy source, and associated transceiver electronics, the insert 100 can transmit measured load data to a receiver for permitting visualization of the level and distribution of load at various points on the prosthetic components. This can aid the surgeon in making any adjustments needed to achieve optimal joint load and balance. Insert 100 further includes a compact low-power energy source.

In general, an insert has at least one articular surface that allows articulation of the muscular-skeletal in conjunction with another prosthetic component. The insert is the wear component of a prosthetic joint and as used today is a passive component with no sensing or measurement capability. The insert is typically made of a solid block of polymer material that is resistant to wear, provides cushioning under loading, and is low friction. The block of polymer material is shaped to fit between other prosthetic components of the artificial joint. One such polymer material used for inserts is ultra-high molecular weight polyethylene.

A joint of the muscular-skeletal system provides movement of bones in relation to one another that can comprise angular and rotational motion. The joint can be subjected to loading and torque throughout the range of motion. A natural joint typically comprises a distal and proximal end of two bones coupled by one or more articular surfaces with a low friction, flexible connective tissue such as cartilage. The natural joint also generates a natural lubricant that works in conjunction with the cartilage to aid in ease of movement. Muscle, tendons, and ligaments hold the joint together and provide motivation for movement. Insert 100 mimics the natural structure between the bones of the joint. In the example, insert 100 has a single articular surface that interfaces with femoral prosthetic component 204 that facilitates articulation of the muscular-skeletal system. A knee joint is disclosed for illustrative purposes but insert 100 is applicable to other joints of the muscular-skeletal system. For example, the hip, spine, and shoulder have similar structures comprising two or more bones that move in relation to one another. In general, insert 100 provides parameter measurement over a range of motion of the muscular-skeletal system.

In the illustrated example, the insert 100 is a uni-condylar knee insert. A uni-condylar knee arthroplasty can be substantially less invasive than a total knee arthroplasty (TKA). People with damage to a single knee compartment or less severe damage to one compartment are candidates for uni-condylar knee arthroplasty. The joint components for the uni-condylar reconstruction comprise the femoral prosthetic component 204, the insert 100, and a tibial prosthetic component 206. One difference that reduces the invasiveness of the uni-condylar surgery is the bone preparation. The distal end of a femur 202 is prepared to receive a femoral prosthetic component 204 that comprises a prosthetic condylar surface or partial condylar surface. Similarly, the proximal end of the tibia 208 is prepared to receive a tibial prosthetic component 206 for supporting and retaining insert sensing device 100. Femoral prosthetic component 204 and tibial prosthetic component 206 can be both trial and permanent prosthetic components. Insert 100 can be used in both the trial and permanent prosthetic components to measure a parameter of the muscular-skeletal system such as loading magnitude and position of loading. The primary surgical modification occurs in a single knee compartment. The remaining knee compartment is untouched or only slightly modified. The patient benefits substantially with the less invasive surgery through reduced pain, quicker recovery time, and partial retention of natural joint function.

It should be noted that the external and interior volume of insert 100 is more constrained in a uni-condylar application than a total knee arthroplasty. The total area and volume for the insert, electronic circuitry, and sensors is greatly reduced in comparison to a dual compartment device. The volume is less than 50% of the volume available for a dual compartment device. For example, the electronics can be shared between each compartment of a dual compartment device by multiplexing between sensors. Moreover, the electronics can be placed between the knee compartments of a TKA insert where this region is not available for the uni-condylar arthroplasty. The insert 100 includes electronic circuitry, a power source, telemetry, antenna, and sensors all housed within and underlying the articular surface. The insert 100 has a form factor substantially equal to a passive final uni-condylar insert such that it can be used as an active final insert having parameter measurement capability.

The height of insert sensing device 100 fits within the bone shaped region of tibia 208 that includes tibial prosthetic component 206 of the knee joint. In the uni-condylar knee arthroplasty example, the surgeon targets a predetermined height or gap during the bone preparation. In one embodiment, the self-contained measurement system comprising insert 100 is less than or equal to 10 millimeters thick. In one embodiment, a small form factor height for the insert 100 of approximately 6 millimeters is achieved. Referring briefly to FIG. 1, support structure 102 having the articular surface 106 and support structure 104 having load-bearing surface 108 are coupled together to form a housing. Interior to the support structures is at least one interior cavity, which houses the self-contained measurement system. As shown, the primary cavity is in the support structure 104. Flexible interconnect couples three sensors to electronic circuitry in the cavity. A power source such as a battery or capacitor powering the electronic circuitry is also in the cavity. A load plate 112 overlies the sensors, electronic circuitry, and power source. The load plate 112 is aligned to the support structure 104 by alignment features 114 and couples to each of the sensors. A port 116 provides access to the interior of insert 100 for sterilizing the cavity. The assemblage height measured from the bottom of the cavity of support structure 104 to the upper surface of load plate measures approximately 4.5 millimeters. The combined wall thickness corresponding to the articular surface and load-bearing surface is approximately 1.5 millimeters such that the height or thickness of insert 100 is approximately 6 millimeters.

Referring back to FIG. 2, the surgeon prepares the surfaces of femur 202 and tibia 208 aligned to the mechanical axis of the leg having a predetermined gap height between the bone surfaces. The predetermined gap height corresponds to the combined thickness of femoral prosthetic component 204, insert 100, and tibial prosthetic component 206. Trial prosthetic components are often used before final prosthetic components are installed to determine if the gap and cuts are appropriate. Adjustments are often made during the trial phase of the surgery.

In the illustration, a surgical procedure is performed to place the femoral prosthetic component 204 onto a prepared distal end of the femur 202. The femoral prosthetic component 204 is a single or partial condyle component. Similarly, a tibial prosthetic component 206 is placed onto a prepared proximal end of the tibia 208. The tibial prosthetic component 206 is a tray or plate affixed to a planarized proximal end of a single compartment of the knee. The bone cuts are made to align the prosthetic components in relation to the mechanical axis of the leg to support and distribute loading. The insert 100 is a third prosthetic component that is placed between tibial prosthetic component 206 and the femoral prosthetic component 204. The three prosthetic components enable the prostheses to emulate the function of a natural knee joint. In the example, insert 100 is used during surgery to take load and load position measurements that can be used to determine prosthetic component fit and to make real-time adjustments to alter load magnitude, load balance, and load position to affect long-term joint performance.

As mentioned previously, insert 100 is inserted between femoral prosthetic component 204 and tibial prosthetic component 206. The articular surface of insert 100 contacts the surface of femoral prosthetic component 204. More specifically, a condylar surface of femur 202 rotates on the articular surface of insert 100 when the tibia 208 is moved in relation to femur 202. The tibial prosthetic component 206 retains the insert 100 and has a corresponding surface that couples to the load-bearing surface of the insert 100. Insert 100 is typically held in a position corresponding to tibial prosthetic component 206 mounted to tibia 208. Typically, tibial prosthetic component 206 has a tray with sidewalls or other features for retaining insert 100 in a fixed position. The muscle, tendons, and ligaments hold the joint together in a manner that applies a compressive force on the articular and load bearing surfaces of insert 100 when installed correctly. The compressive force allows free movement of the joint while retaining the joint in place over the range of motion and under various loadings. Measurement by insert 100 allows precise adjustment such that a force, pressure, or load is set during the trial phase of implantation or when the final prosthetic components are installed. The quantitative measurements are used in conjunction with a surgeon's subjective feedback to ensure optimal fit, position, loading of the prosthesis, and provide verification. The final insert will see a similar loading, balance, and position of applied loading because the final insert and the trial insert are dimensionally substantially equal. It should be noted that insert 100 is designed to be used in the normal flow of an orthopedic surgical procedure without special procedures, equipment, or components. Dimensional equivalence of insert 100 with the final insert simplifies the procedure, allows access for adjustment, and provides compatibility for using the device as an active long-term measurement device to replace the passive inserts being used today. Insert 100 as an active final insert can measure parameters of the muscular-skeletal system with sensors that provide quantitative data on joint status that can be reported to the patient and health care provider.

The insert 100 and the receiver station 210 form a communication system for conveying data via secure wireless transmission within a broadcasting range over short distances on the order of a few meters to protect against any form of unauthorized or accidental query. In one embodiment, the transmission range is five meters or less which will cover a typical operating room. In practice, it can be a shorter distance 1-2 meters to transmit to a display outside the sterile field of the operating room. The transmit distance will be even shorter when device 200 is used in a prosthetic implanted component. Transmission occurs through the skin of the patient and is likely limited to less than 0.5 meters. A combination of cyclic redundancy checks and a high repetition rate of transmission during data capture permits discarding of corrupted data without materially affecting the display of data.

As mentioned previously, insert 100 is substantially dimensionally equivalent to a final insert from an operational perspective. The insert 100 not only fits similarly within the joint as the final insert but also is substantially equivalent from an operational perspective. Operational equivalency ensures that parameter measurements made by insert 100 will translate to the final insert or be equivalent to what is applied to the final insert by the muscular-skeletal system. In at least one embodiment, insert 100 has substantially equal dimensions to the final insert. There can be differences that are non-essential from a measurement perspective between sensor 100 and the final insert. The substantial equal dimensions ensure that the final insert when placed in the reconstructed joint will have similar loading and balance as that measured by insert 100 during the trial phase of the surgery. The substantially equal dimensions also allow fine adjustment such as soft tissue tensioning by providing access to the joint region. Moreover, passive trial inserts of different sizes are commonly used during surgery to determine the appropriate final insert. Thus, the procedure remains the same or similar to the surgeon but with the benefit of quantitative real-time information. It can measure loads at various points (or locations) on the femoral prosthetic component 204 and transmit the measured data to a receiving station 210 by way of an integrated antenna. The receiving station 210 can include data processing, storage, or display, or combination thereof and provide real time graphical representation of the level and distribution of the load.

As one example, the insert 100 can measure forces (Fx, Fy, and Fz) with corresponding locations and torques (e.g. Tx, Ty, and Tz) on the femoral prosthetic component 204 and the tibial prosthetic component 206. It can then transmit this data to the receiving station 210 to provide real-time visualization for assisting the surgeon in identifying any adjustments needed to achieve optimal joint balancing.

In a further example, an external wireless energy source 225 can be placed in proximity to the insert 100 to initiate a wireless power recharging operation. As an example, the external wireless energy source 225 generates energy transmissions that are wirelessly directed to the insert 100 and received as energy waves via resonant inductive coupling. The external wireless energy source 225 can modulate a power signal generating the energy transmissions to convey downlink data that is then demodulated from the energy waves at the insert 100. As described above, the insert 100 is suitable for use as a trial or a permanent knee joint replacement surgery. The external wireless energy source 225 can be used to power the insert 100 during the surgical procedure or thereafter when the surgery is complete and the insert 100 is implanted for long-term use to take periodic measurements of joint status.

In one system embodiment, the insert 100 transmits measured parameter data to a receiving station 210 via one-way data communication over the up-link channel for permitting visualization of the level and distribution of the parameter at various points on the prosthetic components. This, combined with cyclic redundancy check error checking, provides high security and protection against any form of unauthorized or accidental interference with a minimum of added circuitry and components. This can aid the surgeon in making any adjustments needed to optimize the installation. In addition to transmitting one-way data communications over the up-link channel to the receiving station 210, the insert 100 can receive downlink data from the external wireless energy source 225 during the wireless power recharging operation. The downlink data can include component information, such as a serial number, or control information, for controlling operation of the insert 100. This data can then be uploaded to the receiving system 210 upon request via the one-way up-link channel, in effect providing two-way data communications over separate channels. Alternatively, two-way communication through a single channel can be used.

Separating uplink and downlink telemetry eliminates the need for transmit—receive circuitry within the insert 100. Two unidirectional telemetry channels operating on different frequencies or with different forms of energy enables simultaneous up and downlink telemetry. Modulating energy emissions from the external wireless energy source 225 as a carrier for instructions achieves these benefits with a minimum of additional circuitry by leveraging existing circuitry, antenna, induction loop, or piezoelectric components on the insert 100. The frequencies of operation of the up and downlink telemetry channels can also be selected and optimized to interface with other devices, instruments, or equipment as needed. Separating uplink and downlink telemetry also enables the addition of downlink telemetry without altering or upgrading existing chip-set telemetry for the one-way transmit. That is, existing chip-set telemetry can be used for encoding and packaging data and error checking without modification yet remains communicatively coupled to the separate wireless power down-link telemetry operation for download operations herein contemplated. Alternatively, insert 100 can be fitted with a standardized wireless transmit and receive circuitry such as Bluetooth, Zigbee, UWB, or other known wireless systems to communicate with receiver station 210.

As shown, the external wireless energy source 225 can include a power supply 226, a modulation circuit 227, and a data input 228. The power supply 226 can be a battery, a charging device, a capacitor, a power coupling, or other energy source for generating wireless power signals to power the insert 100. The external wireless energy source can transmit energy in the form of, but not limited to, electromagnetic induction, or other electromagnetic or ultrasound emissions. In at least one example embodiment, the wireless energy source 225 includes a coil to electromagnetically couple with an induction coil in insert 100 when placed in close proximity thereto. The data input 228 can be a user interface component (e.g., keyboard, keypad, or touch screen) that receives input information (e.g., serial number, control codes) to be downloaded to the insert 100. The data input 228 can also be an interface or port to receive the input information from another data source, such as from a computer via a wired or wireless connection (e.g., USB, IEEE802.16, etc.). The modulation circuitry 227 can modulate the input information onto the power signals generated by the power supply 226.

Figure 3:
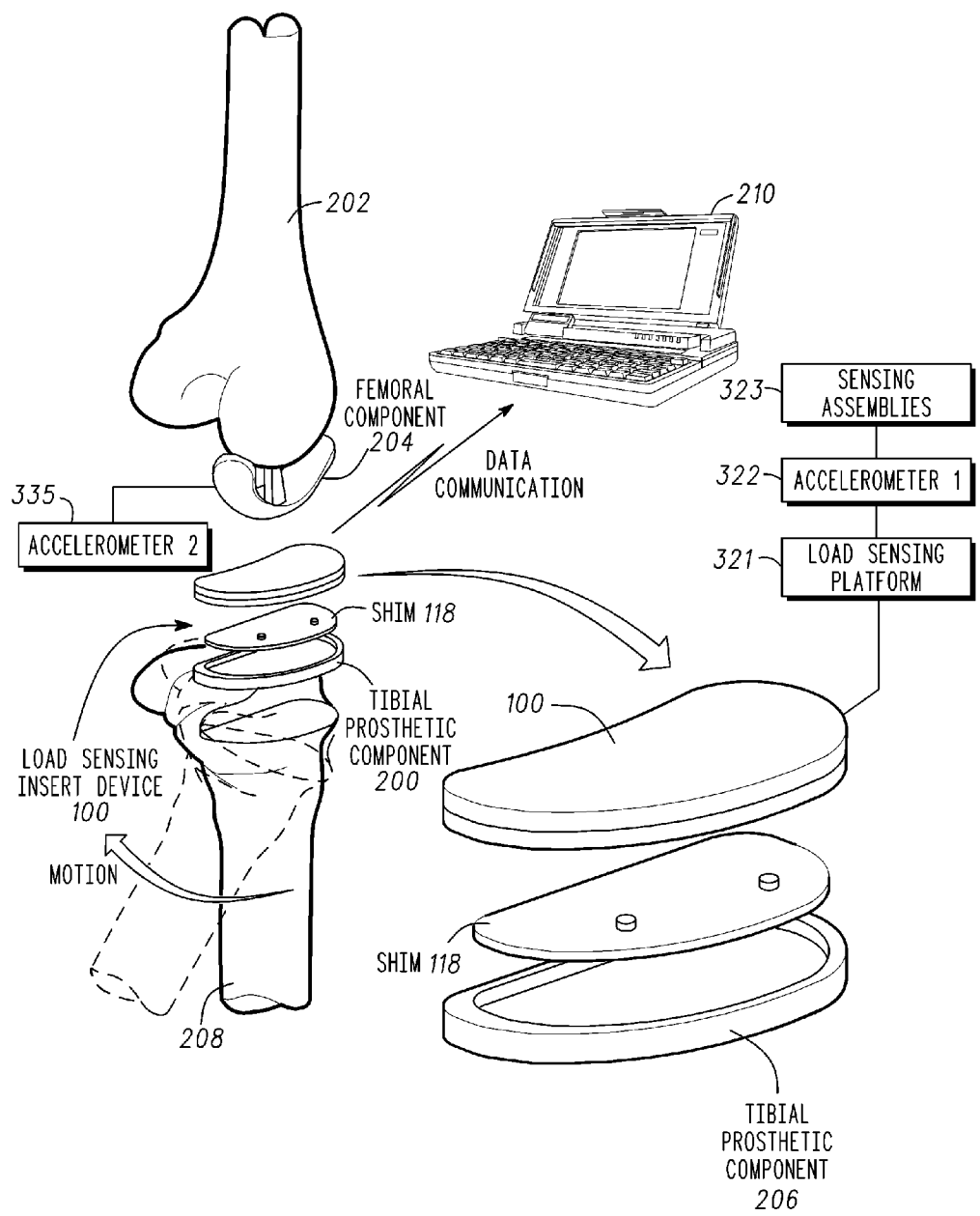
FIG. 3 illustrates the insert placed in a joint of the muscular-skeletal system for measuring a parameter in accordance with an example embodiment.

FIG. 3 illustrates insert 100 placed in a joint of the muscular-skeletal system for measuring a parameter in accordance with an example embodiment. In particular, insert 100 is inserted between femur 202 and tibia 208 for measuring a parameter. In the example, insert 100 includes sensors to measure a force, pressure, or load applied by the muscular-skeletal system. Insert 100 is used to intra-operatively assess a compressive force applied by installed prosthetic components to load-bearing surfaces during the surgical procedure. The insert 100 measures the load magnitude and position of load on the articular surface while transmitting the measured data in real-time by way of wireless data communication to receiver station 210 that can be used for real-time visualization. This provides quantitative data to aid the surgeon in making adjustments to achieve optimal joint loading and the position of the applied load through use of soft tissue tensioning or bone shaping.

A proximal end of tibia 208 is prepared to receive tibial prosthetic component 206. Tibial prosthetic component 206 is a support structure that is fastened to the proximal end of the tibia and is usually made of a metal or metal alloy. In the example, the bone is prepared locally in a specific compartment. The remaining compartment is not modified and is left in a natural state. The tibial prosthetic component 206 retains the insert in a fixed position with respect to tibia 208. The lower major surface of insert 100 is a non-articulating load-bearing surface that couples to the major exposed surface of the tibial prosthetic component 206 that is typically formed as a retention tray.

A distal end of femur 202 is prepared to receive femoral prosthetic component 204. Similarly, bone preparation of femur 202 occurs on the condyle corresponding to the prepared bone surface of tibia 208. The femoral prosthetic component 204 is generally shaped having a condylar surface that interfaces and articulates with insert 100. The bone preparation of femur 202 and tibia 208 is aligned to the mechanical axis of the leg. The upper major surface of insert 100 is an articulating surface that couples with the condylar surface of the femoral prosthetic component 204 allowing movement of the tibia 208 in relation to femur 202. The upper major surface of insert 100 is generally contoured to mate with the prosthetic condylar surface to maximize contact area thereby reducing wear. The lower major surface of insert 100 is a load-bearing surface for distributing loading. The loading on the lower major surface is typically lower than the load applied to the articular surface of insert 100. In one embodiment, the height or thickness of insert 100 can be adjusted during surgery by adding one or more shims of different height. As shown, shim 118 removably attaches to the lower major surface of insert 100. Adding shims increases a height of insert 100 thereby raising the compressive force applied by the joint to the major surfaces of the insert 100 when inserted. Shim 118 when attached to insert 100 has a major surface for interfacing with tibial prosthetic component 206 and being retained therein in a fixed position.

In general, prosthetic components are made in different sizes to accommodate anatomical differences over a wide population range. Similarly, the insert 100 is designed for different prosthetic sizes and shapes. Internally, each sensing device will have similar electronics and sensors. The mechanical layout and structure will also be similar between different sized units. After selecting appropriate sized prosthetic components for the bone structure a remaining variable during trial insertion is the insert height. The height or thickness of insert 100 is adjusted by one or more shims 118. In one embodiment, the gap between the femoral prosthetic component 204 and tibial prosthetic component 206 is approximately 10 millimeters. The insert 100 without a shim typically has a height less than or equal to 10 millimeters. The surgeon selects shim 118 based on the gap between the femur and tibial cuts after preparation of the bone surfaces. The insert 100 of the new predetermined height is then inserted in the knee joint to interact with the femoral prosthetic component 204 and tibial prosthetic component 206. The surgeon may try changing the height or thickness using different shims before making a final decision on the appropriate dimensions of the final insert. Each trial by the surgeon can include modifications to the joint and tissue. The insert 100 allows standardization for a prosthetic platform while providing familiarity of use and installation. Thus, the insert 100 can easily migrate from a trial insert to a final insert that allows long-term monitoring of the joint.

In one embodiment, the insert 100 is used to measure a uni-condylar force, pressure or load in a single compartment of the knee. Data from insert 100 is transmitted to receiving station 210 via wired or wireless communications. The surgeon can view the transmitted information on a display. The effect of an adjustment by the surgeon is viewed in real-time with quantitative measurement feedback from insert 100. The surgeon uses the trial insert to determine an appropriate thickness for the final insert that yields an optimal loading. The absolute loading can be monitored over the entire range of motion or in different points of flexion. In one example usage, insert 100 is removed and modified with a shim if the absolute loading is found to be below a predetermined range. The predetermined range is based on statistical and clinical evidence that produces a positive long-term joint replacement outcome. The height modified insert 100 is then re-inserted into the knee joint. Muscular-skeletal adjustments and shim adjustments can be made until the loading is within the predetermined range. It should be noted that final inserts are available having equal or approximately equal heights and form factor to the shimmed insert 100. The measurement data can be stored for patient personal information or stored in a national database for long-term monitoring of the joint mechanics for improvement thereon.

The position or location of the applied force, pressure, or load occurs on the articular surface can be measured by insert 100 allowing the surgeon to view contact location of the femoral condyle to articular surface over the range of motion on receiving station 210. The position of load can be viewed along a plane or when one bone is rotated in relation to another bone. Typically, it is not desirable for the loading to be towards the outer edge of the articular surface. Insert 100 can identify the position of loading on the articular surface is outside a predetermined area. An adjustment can be made by the surgeon to the bone or prosthetic components that affects where the point of contact occurs on the articular surface or reduces the area of contact over the range of motion. The adjustments can be made in flexion or in extension and tracked by one or more accelerometers. The surgeon can then see in real-time the effect of the modifications on the position of loading on the articular surface over the range of motion. In one embodiment, the trial components are fitted such that the load magnitude falls within the predetermined range and the position of load over the range of motion is within the predetermined area range. The surgeon can affect further change such as load balance by performing soft tissue tensioning. Soft tissue tensioning can increase or decrease the difference in loading between the lateral and medial knee compartments. In one embodiment, the soft tissue tensioning can be performed with insert 100 in place. The change produced by the soft tissue tensioning can be monitored in real-time to show changes in load magnitude on insert 100 due to the modification.

A passive final insert can be fitted between femoral prosthetic component 204 and tibial prosthetic component 206 after quantitative measurement data from insert 100 has been utilized to create an optimized fit of the prosthetic components. The final insert has at least one articular surface that couples to femoral component 204 allowing the leg a natural range of motion. As mentioned above, the final insert has a wear surface that is typically made of a low friction polymer material. Ideally, the prosthesis has a loading, alignment, and balance that mimic a natural leg. It should be noted that insert 100 can be used as a final insert and operated similarly as disclosed herein to provide long-term measurements via sensors therein. The wear surface if active insert 100 can comprise one or more layers of low friction polymer material such as ultra high molecular weight polyethylene. The wear surface can be bonded or attached to a housing of insert 100 to form the articular surfaces. Alternatively, the upper and lower support structures that form a housing or enclosure can be molded or machined from the low friction polymer material.

In one embodiment, insert 100 used intra-operatively is a low cost disposable system that reduces capital costs, operating costs, facilitates rapid adoption of quantitative measurement, and initiates evidentiary based orthopedic medicine. In a second embodiment, a methodology of reuse can be implemented through sterilization. Two embodiments, are disclosed herein where the cavity within the insert is sterilized and where the cavity is not sterilized in a sterilization process. In a third embodiment, can be incorporated in a tool, muscular-skeletal system, or the other prosthetic trial components than the insert. In a fourth embodiment, insert 100 can be a permanent component of the replacement joint. Insert 100 can be used to provide both short term and long term post-operative data on the implanted joint. In a fifth embodiment, insert can be coupled to the muscular-skeletal system in a non-joint application for parameter measurements. In all of the embodiments, receiving station 210 can include data processing, storage, or display, or combination thereof and provide real time graphical representation of the level and distribution of the load. Alternatively, an indicator can be placed on insert 100 that states whether the loading is high, low, or within the predetermined range (e.g. different color LEDs). Receiving station 210 can record and provide information generated by insert 100 to a secure database.

The insert 100 comprises a load-sensing platform 321, an accelerometer 322, and sensing assemblies 323. This permits the insert 100 to assess a total load on the prosthetic components as the joint is taken through the range of motion. The system accounts for forces due to gravity and motion. In one embodiment, load-sensing platform 321 includes an articular surface, a load plate, load-sensing assemblies 323, and electronic circuitry. The accelerometer 322 of insert 100 measures acceleration. Acceleration can occur when the insert is moved or put in motion. Accelerometer 322 senses orientation, vibration, and impact. In another embodiment, the femoral component 204 can similarly include an accelerometer 335, which by way of a communication interface communicates to the insert 100, thereby providing reference position and acceleration data to determine an exact angular relationship between the femur 202 and tibia 208. In one embodiment, sensing assemblies 323 comprise at least three sensors coupled at predetermined locations to the load plate. The load plate distributes the load applied to the articular surface to sensing assemblies 323. Together the load sensing platform 321, accelerometer 322, accelerometer 335, and sensing assemblies 323 provide quantitative information on relative position, position, load, and location of the applied load that can be used by the surgeon for optimal installation of the prosthetic components.

Incorporating data from the accelerometer 322 assures accurate measurement of the applied load, force, pressure, or displacement by enabling computation of adjustments to offset external motion. This capability can be required in situations wherein the body, instrument, appliance, vehicle, equipment, or other physical system, is itself operating or moving during sensing of load, pressure, or displacement. This capability can also be required in situations wherein the body, instrument, appliance, vehicle, equipment, or other physical system, is causing the portion of the body, instrument, appliance, vehicle, equipment, or other physical system being measured to be in motion during sensing of load, pressure, or displacement.

The accelerometer 322 can operate singly or as an integrated unit with the sensing assemblies 323. Integrating one or more accelerometers 322 within the sensing assemblages 323 to determine position, attitude, movement, or acceleration of sensing assemblages 323 enables augmentation of presentation of data to accurately identify, but not limited to, orientation or spatial distribution of load, force, pressure, displacement, density, or viscosity, or localized temperature by controlling the load and position sensing assemblages to measure the parameter or parameters of interest relative to specific orientation, alignment, direction, or position as well as movement, rotation, or acceleration along any axis or combination of axes. Measurement of the parameter or parameters of interest may also be made relative to the earth's surface and thus enable computation and presentation of spatial distributions of the measured parameter or parameters relative to this frame of reference.

In one embodiment, the accelerometer 322 includes direct current (DC) sensitivity to measure static gravitational pull with load and position sensing assemblages to enable capture of, but not limited to, distributions of load, force, pressure, displacement, movement, rotation, or acceleration by controlling the sensing assemblages to measure the parameter or parameters of interest relative to orientations with respect to the earths surface or center and thus enable computation and presentation of spatial distributions of the measured parameter or parameters relative to this frame of reference.

As mentioned previously, insert 100 can be used for other joint surgeries; it is not limited to knee replacement implant or implants. Moreover, insert 100 is not limited to trial measurements. Insert 100 can be incorporated into the final joint system to provide data post-operatively to determine if the implanted joint is functioning correctly. Early determination or identification of problem can reduce catastrophic failure of the joint by bringing awareness to a problem that the patient cannot detect. The problem can often be rectified with a minimal invasive procedure at lower cost and stress to the patient. Similarly, longer term monitoring of the joint can determine wear or misalignment that if detected early can be adjusted for optimal life or replacement of a wear surface with minimal surgery thereby extending the life of the implant. For example, increasing load magnitude over time on the articular surface is an indicator of improper wear and alignment. In general, insert 100 can be shaped such that it can be placed or engaged or affixed to or within load articular surfaces used in many orthopedic applications related to the musculoskeletal system, joints, and tools associated therewith. Insert 100 can provide information on a combination of one or more performance parameters of interest such as wear, stress, kinematics, kinetics, fixation strength, ligament balance, anatomical fit and balance.

Figure 4:
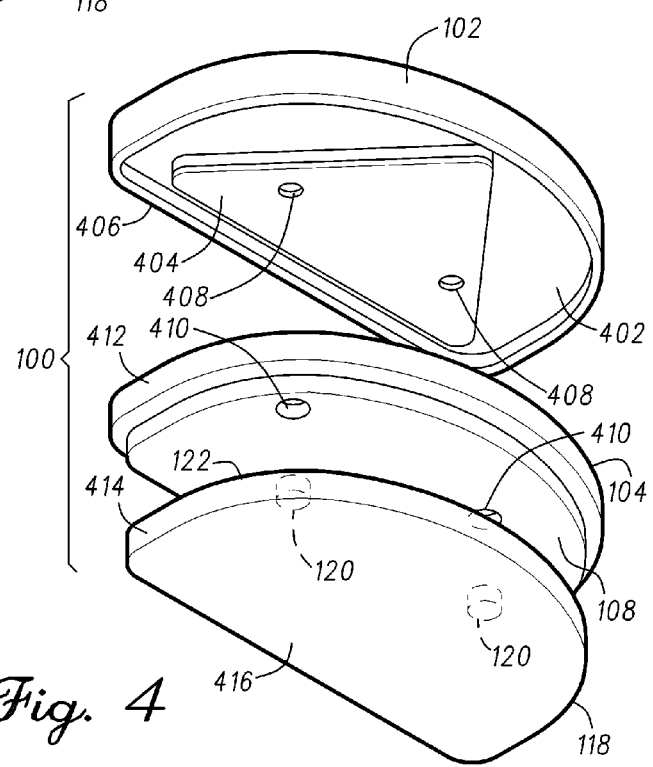
FIG. 4 illustrates surfaces of the insert in accordance with an example embodiment.

FIG. 4 illustrates surfaces of insert 100 in accordance with an example embodiment. Internal to insert 100 is a measurement system for measuring or monitoring the muscular-skeletal system. In the example, insert 100 can be changed to have varying height or thickness and measure a force, pressure, or load. Insert 100 forms a housing for the measurement system when support structures 102 and 104 are coupled together. The housing includes a self-contained parameter measurement system. The height or thickness is adjusted by one or more shims. In the illustration, shim 118 attaches to support structure 104 for increasing a height of insert 100. Support structure 102 has an articular surface (not shown) allowing articulation of the muscular-skeletal system. The housing formed by support structures 102 and 104 includes electronic circuitry, a power source, and sensors comprising a complete self-contained system for measuring a parameter of the muscular-skeletal system such as a force, pressure, or load applied to the articular surface. The insert 100 can have a display to indicate the measured parameter or wirelessly transmit the data for further data processing and enhanced user interface.

For illustrative purposes, insert 100 is a uni-condylar knee insert for uni-condylar knee reconstruction. The articular surface corresponds to a single compartment of the knee. In one embodiment, the articular surface is concave for interfacing with a prosthetic femoral condyle surface. A major interior surface 402 of upper support structure 102 includes a region 404 that interfaces with a load plate of the sensor assembly. The region 404 can include alignment features 408 for aiding in alignment of support structure 104 to support structure 102. In the example, the alignment features 408 are holes or openings. The upper support structure 102 further includes a peripheral region 406 having a surface that interfaces with a corresponding surface of support structure 104. The peripheral region 406 and the corresponding surface of support structure 104 seal one or more cavities within insert 100 from an external environment when coupled together. The surfaces can be sealed mechanically or through the use of sealants. In the example, a sealant is used to attaches the peripheral surfaces of support structures 102 and 104 together. The interior of structures 102 and 104 can be hermetically sealed from the external environment using the sealant, welding, or bonding process. In one embodiment, the bond of the peripheral surfaces is so strong that the housing would be broken by an attempt to disassemble or separating support structures 102 and 104. This is beneficial when insert 100 is a disposable device for use in a single application.

In the example, the uni-condylar tibial prosthetic component when installed can have an exposed tray or surface for receiving and retaining insert 100. Insert 100 can have features that engage with the tibial prosthetic component to aid in retention. In one embodiment, the load-bearing surface 108 has a planar region that interfaces with a planar region of the tibial tray of the tibial prosthetic component. The interface between the load-bearing surface 108 and the planar region of the tibial tray distributes the load over the area where the devices couple together. Typically, the area where the tibial tray and insert 100 couple together is greater than a corresponding area where the prosthetic femoral condyle couples to the articular surface of support structure 102. Thus, load per unit area on surface 108 is substantially lower than the loading on the articular surface of support structure 102 through distribution of the load over a larger area.

The minimum height of insert 100 comprises support structures 102 and 104 without shim 118. As mentioned previously, insert 100 has been fabricated having height or thickness less than 10 millimeters, which is suitable for most of the population requiring implants. Reducing the height and form factor promotes further integration into tools, equipment, prosthetic components, and direct implants. In the uni-condylar application, insert 100 has been fabricated having a height or thickness of approximately 6 millimeters. The sensing assembly within the interior of insert 100 has a height or thickness of less than 5 millimeters. The overlying and underlying support surfaces of insert 100 can have a thickness of approximately 0.5 millimeters in the intra-operative measurement device. Insert 100 is substantially dimensionally equal in shape and size to a final insert. In the example, shim 118 is a passive device of insert 100 for adjusting insert height. In one embodiment, prior to inserting insert 100, the knee joint is prepared by a surgeon having trial or permanent femoral and tibial prosthetic components. As mentioned previously, the benefit of the uni-condylar surgery is that a knee compartment is kept in a natural state. The initial bone cuts and preparation are made on a single compartment, which is a much less invasive procedure. The uni-condylar operation typically requires a smaller form factor when compared to a dual compartment insert thus placing a premium on reducing height, area, and volume of insert 100. Insert 100 is used with both trial and final femoral and tibial prosthetic components. The gap left between the tibial and femoral prosthetic components is greater than or equal to the height or thickness of insert 100 without shim 118.

A force can be applied to insert 100 to place the device between the femoral and tibial prosthetic components. A peripheral region 412 of support structure 104 has a surface that couples to the surface of peripheral region 406 of support structure 102. The peripheral region 412 is a sidewall that extends around the periphery of support structure 104. Shim 118 couples to support structure 104 such that the load bearing surface of shim 118 is similar to the load bearing surface of support structure 104. The impact force applied to insert 100 inserts the prosthetic component in the tray of tibial prosthetic component such that the tray retains peripheral region 412, a sidewall 414 of shim 118, or both. The muscle, ligaments, and tendons stretch to accommodate placement of the insert 100 in the joint and retract once the prosthetic component is seated between the tibia and femur. The muscle, ligaments, and tendons apply a compressive force on the insert 100. Surgically, the gap between the trial or final prosthetic components is designed by the surgeon to be approximately the height or thickness of insert 100 such that a shim can be used to generate a predetermined compressive force on the articular surface of insert 100 after insertion. Insert 100 can be removed from the tibial tray allowing shim replacement to adjust height. Shims of different heights or thicknesses, such as shim 118, are removed and replaced until an appropriate thickness for the final insert is selected using the quantitative measurements provided therewith. The knee is placed in flexion to remove insert 100. In further embodiment, the height or thickness of insert 100 is selected to measure higher than optimal when inserted. In one embodiment, insert 100 is a trial insert that is used to assess and select a final insert. Insert 100 is dimensionally substantially equal to the final insert allowing access to the joint for further optimization processes. Soft tissue tensioning can be used to adjust absolute magnitude of the uni-condylar prosthesis. Similarly, soft tissue tensioning can be used to adjust balance between compartments.

As disclosed above, shim 118 is attachable to the load bearing surface 108 of insert 100. Shim 118 has major surfaces 122 and 416 that are load-bearing surfaces. Shim 118 has a predetermined height or thickness. The predetermined height or thickness of shim 118 is the distance between major surfaces 122 and 416. Major surface 122 of shim 118 interfaces with load-bearing surface 108 of support structure 104. In the example, shim 118 can be temporarily attached to support structure 104. In the embodiment, features 120 extend from major surface 122 and are shaped to fit in openings 410 of support structure 104. Although described as cylindrical, the features can have shape and taper that aid in alignment, retention, and removal. For example, a T-shaped feature could be used such that only a single orientation would allow coupling of shim 118 to support structure 104. Shim 118 is inserted into the corresponding openings 410 in load-bearing surface 108 until the major surface 122 interfaces with load-bearing surface 108. In one embodiment, features 120 have a friction fit with openings 410. The height of insert 100 is the combined height or thickness of support structure 102, support structure 104, and shim 118. In the example, the clearance or interference fit allows shim 118 to be separated from support structure 104 with little resistance. The use of shims allows rapid changing of the height of insert sensing device 100. The surgeon has both subjective and quantitative measurement to assess the installation. The feedback is provided throughout the range of joint motion with insert 100 inserted. Finally, the insert 100 allows fine-tuning of the loading and balance within suggested predetermined ranges based on historical data. In one embodiment, the predetermined ranges for measured loading would be based on analysis of a large number of intra-operative and long-term quantitative measurements using sensored systems such as disclosed herein and related to operation of the prosthesis.

Figure 5:
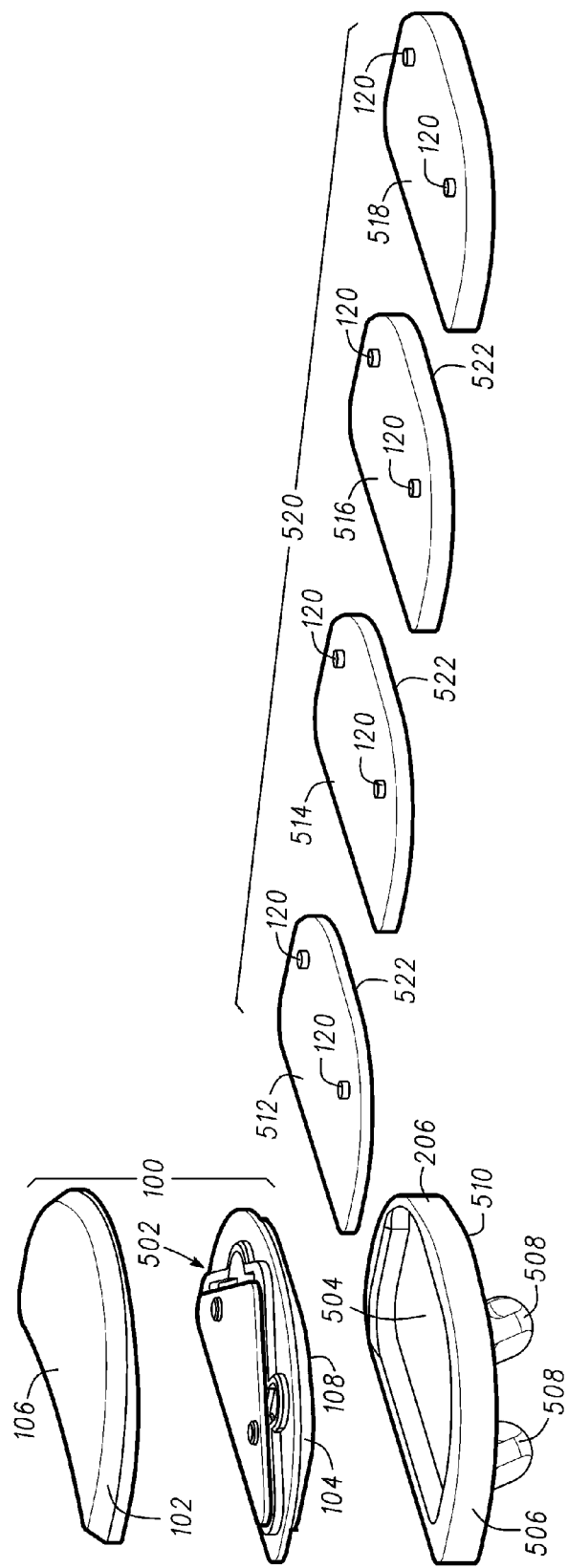
FIG. 5 illustrates the insert and a plurality of shims in accordance with an example embodiment.

FIG. 5 illustrates insert 100 and a plurality of shims 520 in accordance with an example embodiment. It should be noted that when discussing the measuring system, the term insert 100 can include an attached shim but at a minimum comprises support structure 102 coupled to support structure 104 with active measurement circuitry therein. A sensing assembly 502 comprises at least one sensor and electronic circuitry. In the example, sensing assembly 502 is housed within insert 100 with a power source and a load plate for distributing a force, pressure, or load to multiple sensors. As shown, insert 100 includes sensors that are coupled to the articular surface 106 through the load plate of sensing assembly 502. In one embodiment, three sensors are used to measure the load magnitude and the location where the load is applied to articular surface 106.

The tibial prosthetic component 206 comprises a support surface 510, sidewalls 506, and features 508. As shown, tibial prosthetic component 206 is used for a uni-condylar knee application. The support surface 510 interfaces with a prepared bone surface of a proximal end of the tibia. Extending from the support surface 510 are features 508. Features 508 locate and retain the tibial prosthetic component 206 to the prepared tibia bone surface in a fixed location. Features 508 fit into corresponding openings of the prepared tibia bone surface. Sidewall 506 is formed on the periphery of tibial prosthetic component 206 such that a cavity 504 is formed. Cavity 504 has a predetermined shape that corresponds to the shape of support structure 104 and shims 520. The load-bearing surface 108 or the surface 522 of shims 520 interface with the surface of the tray of tibial prosthetic component 206 when inserted therein. An alternative to cavity 504 is one or more features on insert 100 and tibial prosthetic component 206 that engage to retain insert 100 in place when tibial prosthetic component 206 does not have sidewall 506.

As shown, shims 520 comprises shims 512, 514, 516, and 518. In the example, each shim has a different height or thickness. A system can comprise more or less than the number of shims shown. Shims 520 include features 120 for attaching to a load-bearing surface 108 of support structure 104. Support structure 104 has corresponding openings for receiving features 120. In one embodiment, shims 520 comprise a solid material such as plastic that does not deform or change height under loading. Alternatively, shims 520 can have cavities to reduce the amount of material used. For example, shim 520 can have hexagonal shaped cavities with the walls of the hexagonal cavities supporting the loading. The hexagonal wall structure would be more than sufficient to support and distribute the loading applied to insert 100 while reducing the amount of material used. Each shim of shims 520 in combination with the height of support structures 102 and 104 corresponds to an available final insert thickness.

The appropriate device size is determined by loading and position of load measured by sensing assembly 502. In the example, an appropriate height is determined when the load magnitude and position of applied loading on articular surface 106 is respectively within a predetermined load magnitude range and a predetermined area range on articular surface 106. Insert 100 is removed if the measurements are outside either range. The knee can be placed in flexion to allow access to remove insert 100. A shim can be used to increase or decrease height of insert 100 to respectively raise or lower the load magnitude reading. Also, modifications to the muscular-skeletal system or prosthetic components can be performed for adjustment to the area of applied loading or load magnitude. In one embodiment, once a suitable height has been identified insert 100 is disposed of. The final insert of the identified height is inserted into the joint having the same height or thickness as the trial insert. Fine adjustments such as soft tissue tensioning can be made prior to or after the selection of the height of the final insert. The final insert can be passive or have active circuitry for measuring parameters of the final insert or the knee joint region. In general, the load and position of load throughout the range of motion on the final insert is similar to that of the previously removed insert 100. It should be noted that the number of shims 520 in a kit provided for installation of a uni-condylar joint replacement can be more or less than shown in the illustration. The number of different height availability will depend on the needs of the specific muscular-skeletal application.

Figure 6:
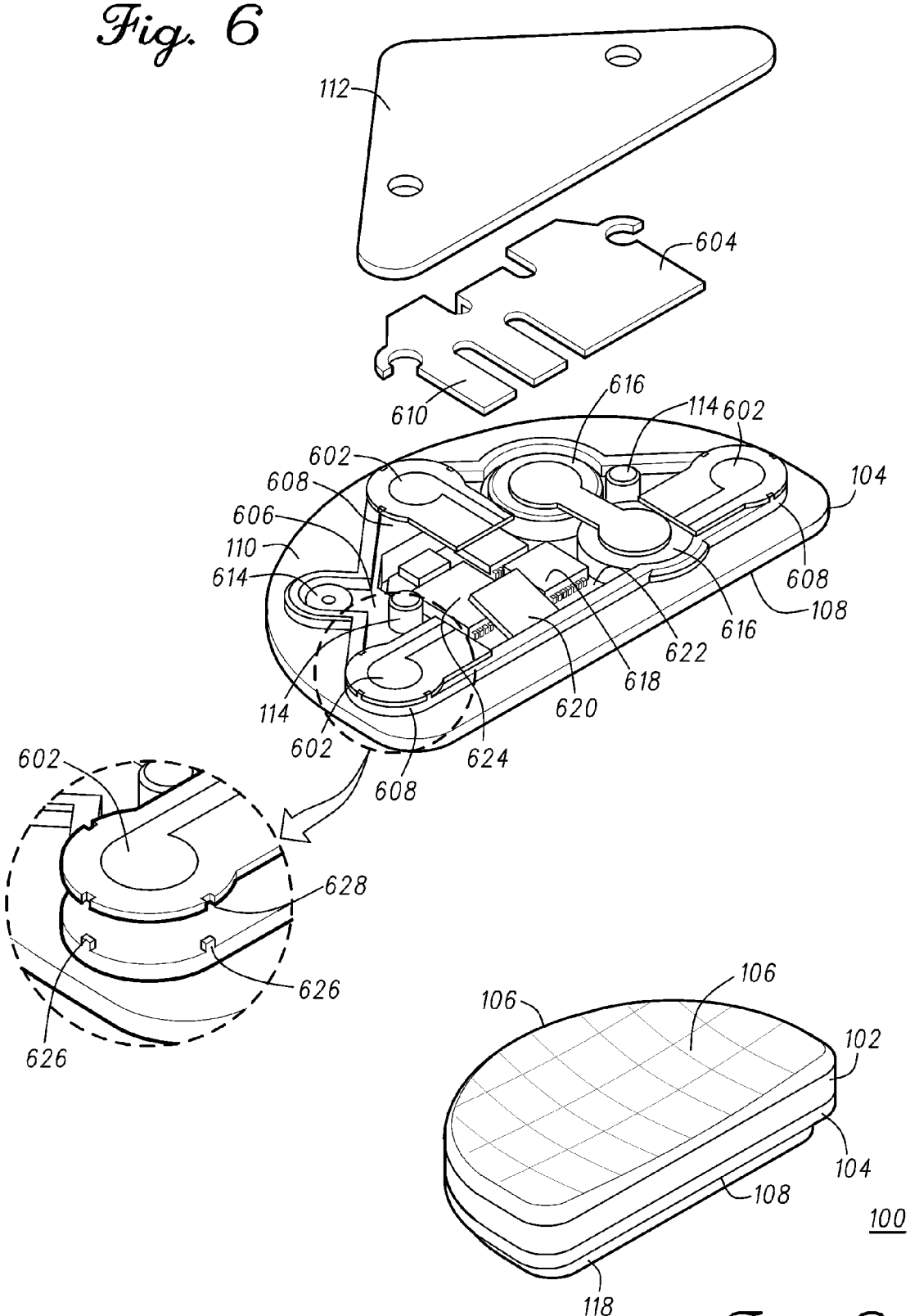
FIG. 6 illustrates the lower support structure of the unicondylar insert in accordance with an example embodiment.

FIG. 6 illustrates lower support structure 104 of the uni-condylar insert 100 in accordance with an example embodiment. An upper support structure (not shown) has at least one bearing or articular surface to allow movement of the muscular-skeletal system. The upper support structure fastens to the lower support structure 104 to form a sealed enclosure or housing. The sealed enclosure protects active circuitry of insert 100 for parameter measurement to aid in prosthetic installation, muscular-skeletal parameter measurement or long-term monitoring of a reconstructed joint. The entire measurement system is self-contained within the upper and lower support structure. The insert 100 is substantially equal dimensionally to a final passive insert. As shown, the measurement system fits within the dimensions of a uni-condylar prosthetic insert. In the example, the enclosure houses multiple sensors for measuring the magnitude and position of loading applied to a compartment of the knee.

The active system of the insert comprises sensors 602, interconnect 604, one or more printed circuit boards 622, electronic circuitry 618, and a power source 616. The electronic circuitry 618 is mounted on printed circuit board 622. The electronic circuitry 618 comprises power management circuitry, measurement circuitry, digital logic, parameter conversion circuitry, ND converters, D/A converters, and transmit/receive circuitry. In one embodiment, an application specific integrated circuit (ASIC) 624 customized for muscular-skeletal parameter sensing application is utilized. The ASIC 624 reduces the number of components that mount to printed circuit board 622. The integration of circuitry onto an ASIC eliminates unneeded circuitry, adds circuitry specific to parameter measurement, reduces power consumption of the measurement system, and reduces the sensing system form factor to a size that fits within a prosthetic component. Similarly, the printed circuit board 622 reduces the form factor allowing for placement within a uni-condylar insert. In one embodiment, the printed circuit board 622 has multiple layers of interconnect for interconnecting components. The printed circuit board 622 can have components mounted on both major surfaces to further reduce the form factor. An antenna can also be formed on printed circuit board 622 for short-range transmission of the measurement data. A fully populated printed circuit board 622 with power source 616 has been manufactured that has a height or thickness equal to or less than 3.5 millimeters.

The power source 616 powers electronic circuitry 618 and sensors 602. In one embodiment, the power source 616 comprises one or more batteries. As shown, two batteries are coupled to the printed circuit board 616. In one embodiment, the two batteries are coupled in series. In the intra-operative example, the measurement system is disposed of after the surgery is completed or when the batteries are depleted. Alternatively, a rechargeable system can power electronic circuitry 618. The power source 616 can be a rechargeable battery, capacitor, or other temporary power source. The power source 616 can be electro-magnetically coupled to a remote power source for receiving charge. In the remote charging example, the power source 616 and power management circuitry enables the measurement system for parameter measurement after sufficient charge is stored to perform a measurement process. It should be noted that the power consumption reduction due to the ASIC enables the use of rechargeable methodologies such as the capacitor. The capacitor provides the further benefit of extended life and no chemicals when compared with batteries for a long-term implant application such as joint monitoring.

In the example, the measurement system measures the load magnitude and load position that the muscular-skeletal system applies to the articular surface of the upper support structure. The uni-condylar insert includes three sensors 602 for load and position measurement. In one embodiment, each sensor 602 is a piezo-resistive film sensor. The resistance of a piezo-resistive film changes with an applied pressure. A resistance, voltage, or current corresponding to the piezo-resistive film under load is measured. The measured resistance, voltage, or current is then correlated back to a pressure measurement. It should be noted that sensor types such as continuous wave, pulsed, pulsed echo, strain gauge, polymer, mechanical, film, and mems to name but a few can also be used. The piezo-resistive sensor 602 being a film type sensor has a small form factor from a depth perspective. The contact area of sensor 602 in one embodiment is approximately 3.175 square millimeters. The load applied to the articular surface is transferred through the load plate 112 to sensors 602 thereby compressing the film and modifying the resistance thereof. The amount of compression can vary depending on the selected film type. In general, the change in height of the sensor assembly is negligible measuring less than 0.2 millimeters for some sensor types. In one embodiment, piezo-resistive film for measuring loading in a uni-condylar application compresses approximately 0.508 millimeters over the expected load range for an intra-operative application.

In a second embodiment, a transit time is correlated to the pressure measurement. Transit time measurements correspond to continuous wave, pulsed, and pulsed echo measurements. Transit time measurements can be very accurate when taking a large number of measurements. An ultrasonic continuous wave or pulsed signal is propagated through a compressible waveguide. Loading on the insert compresses the compressible waveguide thereby changing the length of the waveguide. A change in length corresponds to a change in transit time. The transit time can be related to a frequency by holding the number of waves in the compressible waveguide to a fixed integer number during a measurement sequence. Thus, measuring the transit time or frequency allows the length of the waveguide to be precisely measured. The pressure can be calculated with knowledge of the length versus applied pressure relationship of the waveguide.

The three sensors 602 underlie the bearing or articular surface of the upper support structure. Sensors 602 of each compartment are located at predetermined positions on lower support structure 104. In the example, each sensor 602 overlies a corresponding pad region 608 as part of support structure 104. The pad regions 608 can have a predetermined area that couples to a corresponding sensor 602. Measurements from each of the sensors 602 are used to determine the location of applied loading to the articular surface. The electronic circuitry 618 can take measurements sequentially or in parallel. The location and magnitude of the applied load is determined by analysis of the magnitudes from each of the three sensors 602. The analysis includes a differential comparison of the measured loads. In general, the location of the applied load is closer to the sensor reading the highest load magnitude. Conversely, the applied load will be farthest from the sensor having the lowest load magnitude. The use of sensors 602 at predetermined positions allows the applied load location to calculated using the measured load magnitudes from each of sensors 602.

The support structure 104 further comprises peripheral surface 110, a cavity 606, features 114, and a port 612. The peripheral surface 110 mates with a corresponding surface of the upper support structure when coupled together to form a housing. Features 114 extend from support structure 104. Features 114 align the support structure 104 to the upper support structure. The upper support structure has corresponding openings to receive features 114. The cavity 606 underlies the articular surface of the upper support structure. Cavity 606 can have features or structures for aligning and retaining printed circuit board 622 in place. The uppermost surface of printed circuit board 622 and components mounted thereon when placed in cavity 626 is approximately equal to or below a surface of pad regions 608.

As shown, pad regions 608 are placed in regions corresponding to vertexes of a triangle. In one example, two sides of the triangle formed by pad regions 608 are equidistant from the coronal plane having a length of approximately 19 millimeters. The third side of the triangle is approximately 38 millimeters in length. As mentioned previously, sensors 602 are placed on pad regions 608. The pad regions 608 can have features to retain and align the sensors 602 in predetermined positions. An expanded view of pad region 608 and sensor 602 shows features 626 as tabs on a periphery of pad region 608. Features 626 extend upward from pad region 608. Sensor 602 has notches 628 corresponding to features 626. Sensor 602 can be placed on pad region 608 to engage with features 626 to retain and align sensor 602 to pad region 608, interconnect 604, and load plate 112. In one embodiment, sensors 602 have a predetermined area for coupling to the articular surface and sensing a load applied thereto. The pad regions 608 have an area equal to or larger than the predetermined area of sensors 602. The predetermined area of sensors 602 is selected to distribute the load over sufficient area for reliable sensing, provide a measurable signal (e.g. voltage, current, resistance) over the loading range, and have the sensitivity for precise measurement. The predetermined area and location is sufficiently small to allow accurate identification of the load location based on the measurements from the three locations.

The interconnect 604 overlies a portion of the printed circuit board 622 and portions of sensors 602. The interconnect 604 includes cut away sections for receiving features 114. Features 114 couple through the cut away sections of interconnect 604 thereby aligning and retaining the structure. Conductive traces on interconnect 604 interface with conductive traces on sensors 602 for coupling to electronic circuitry 618. A connector 620 is coupled to components on printed circuit board 622. A tab 610 having conductive traces is inserted into connector 620 for coupling electronic circuitry 618 to sensors 602. The load plate 112 overlies the interconnect 604 and sensors 602. The load plate couples to sensors 602. In the example, load plate 112 is approximately triangular in shape. Load plate 112 distributes the force, pressure, or load applied to the articular surface to sensors 602. Support structure 104 further includes a port that will be disclosed hereinbelow. The port is a path for providing a sterilizing gas into cavity 606. A seal 614 includes a gas permeable membrane such that gas can pass into cavity 626 but liquid and solids are blocked from entering.

Figure 7:
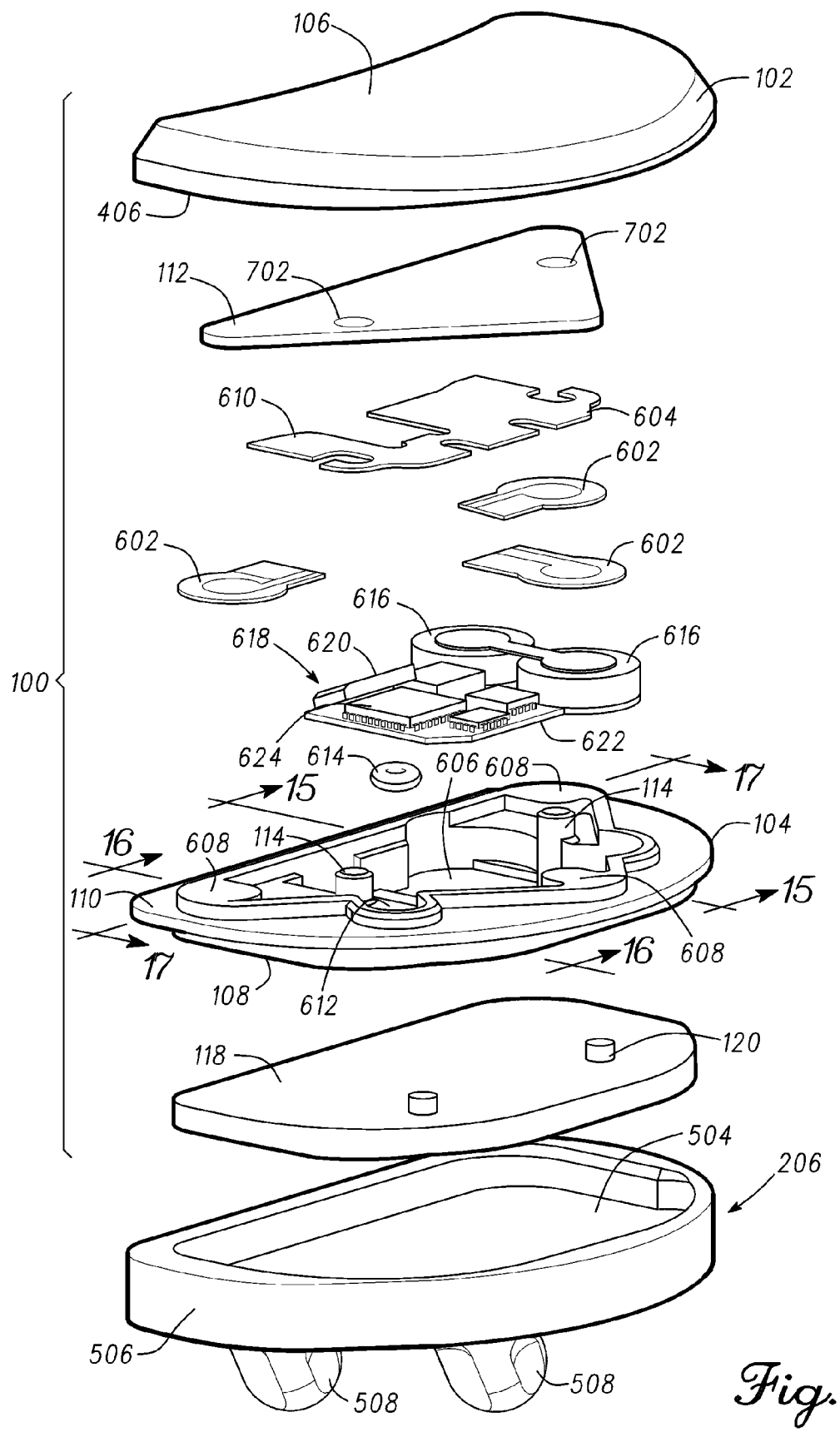
FIG. 7 illustrates the components of the insert in accordance with an example embodiment.

FIG. 7 illustrates the components of insert 100 in accordance with an example embodiment. Support structure 104 includes pad regions 608 that support sensors 602. In the example, three pad regions 608 and three corresponding sensors 602 are used to determine location of applied load to the articular surface 106 of insert 100. In one embodiment, the pad regions 608 have a predetermined area and can include features to retain a sensor. The predetermined area is selected to provide sufficient area for monitoring a signal magnitude and differential signal changes within the resolution required for the muscular-skeletal application. Pad regions 608 are a predetermined height above the load-bearing surface 108 of support structure 104. The predetermined height is chosen to ensure that the electronic circuitry 618 does not interfere with the application of load to the articular surface 106 as will be discussed in greater detail hereinbelow. In one embodiment, a sidewall directs and retains the sensor 602 in the predetermined area and in a predetermined orientation. The features can orient the sensor lead to allow coupling with interconnect 604 during an assembly process.

In the uni-condylar example, the electronic circuitry 618 partially or completely underlies a region where loading is applied to the articular surface 106. Electronic circuitry 618 is located centrally within support structure 104 in the cavity 606. The electronic circuitry 618 is mounted to and interconnected by patterned metal interconnect on printed circuit board 622. The power source 616 and connector 620 are mounted to printed circuit board 622. In the example, the power source 616 comprises batteries that power the measurement system for a single application. The printed circuit board 622 and cavity 606 can have a predetermined shape that allows a singular orientation for placement therein. Cavity 606 can include support structures and retaining features to support and retain electronic circuitry 618 in place. To reduce form factor the printed circuit board 622 or components mounted thereon can contact an interior surfaces of the cavity 606. Alternatively, the printed circuited board 618 and components have a small gap between the interior surfaces of cavity 606. In one embodiment, the pad regions 608 are co-planar to one another at the predetermined height above the load-bearing surface 108 of support structure 104. The uppermost surface of printed circuit board 622, electronic circuitry 618, and power source 616 is below sensors 606 when placed in cavity 606. More specifically, under maximum compression (or maximum loading) of sensors 602 the interconnect 604 or load plate 112 would not make contact with the measurement system electronics. Similarly, if the pad regions 608 were not co-planar to one another, the system electronics would be below the sensor 602 having the pad region 608 of the lowest height above the load-bearing surface 108.

A sensing assembly stack of insert 100 comprises the load plate 106, sensors 602, and pad regions 608. The pad regions 608 are arranged to be at the vertexes of a triangle. In the example, the majority of cavity 606 is between and within the bounds of the triangle defined by pad regions 608. As mentioned previously, the electronic circuitry 618, power source 616, and printed circuit board 622 are placed in cavity 606. The sensors 602 are placed on pad regions 608. In the example, sensors 602 are piezo-resistive film sensors that changes resistance due to a pressure applied thereto. Interconnect 604 overlies and couples to each sensor 602. As mentioned previously, the pad regions 608 are co-planar to one another. The interconnect 604 can be flexible but is planar to connect to sensors 602. At least a portion of interconnect 604 overlies electronic circuitry 618, printed circuit board 622, and power source 616. The alignment features 114 couple through openings in interconnect 604 to align interconnect 604 to sensors 602. The tab 610 of interconnect 604 is a flexible connector. Tab 610 couples to connector 620 on printed circuit board 622 thereby coupling sensors 602 to electronic circuitry 618. The load plate 112 is coupled to an interior of surface of the support structure 102. The alignment features 114 couple through openings 702 to align load plate 112 to sensors 602. The vertices of load plate 112 couple to sensors 602. At least a portion of load plate 112 overlies electronic circuitry 618, printed circuit board 622, and power source 616. Finally, an interior surface of support structure 102 couples to load plate 112. In one embodiment, the coupled interior surface of support structure 102 is shaped similar to that of load plate 112. The interior surface of support structure 102 includes openings to receive alignment features 114 to align support structure 102 to support structure 104. The surface 406 of support structure 102 and the surface 110 of support structure 104 are coupled together either permanently or temporarily to seal the cavity 606 and components therein from an external environment.

In general, a load applied to the articular surface 106 couples through support structure 102 to the interior surface where it is applied to the sensing assembly stack. The load plate 112 distributes loading from the interior surface of support structure 102 to the three sensors 602. Each sensor 602 provides a measurement to electronic circuitry 618 through interconnect 604. The magnitude of the applied load to articular surface 106 is calculated from the three measurements. Similarly, the location where the load is applied on the articular surface 106 is calculated using each sensor measurement and the location of each sensor relative to articular surface 106.

FIG. 8 illustrates assembled insert 100 in accordance with an example embodiment. Components from FIG. 7 will also be referred to in the description. Insert 100 is substantially equal in dimensions to a passive final insert and can be used similarly. The passive final insert has no measurement capability and is a long-term or permanent insert for a muscular-skeletal joint. Insert 100 can be used intra-operatively to aid in the assessment, installation, and optimization of a joint of the muscular-skeletal system or as an active final insert for providing joint information long-term. For example, insert 100 as an active final insert can be used to measure insert wear, loading, position of loading, infection, and joint range of motion. In one embodiment, insert 100 is activated by charging a capacitor for powering the measurement system. The capacitor holds sufficient charge to perform the required measurement sequences and wirelessly send the data to an appropriate source for analysis. The quantitative loading and position of loading measurements can be used if a misalignment or contact surface issue arises that could cause accelerated joint failure. Knowledge of changes in the joint can be used to correct the joint problems before a catastrophic failure or major invasive surgery is required.

As shown, support structure 102 and support structure 104 are fastened together forming active insert 100. The major exposed surfaces of support structures 102 and 104 are respectively articular surface 106 and load-bearing surface 108. Although shown as a uni-condylar knee insert, the form factor disclosed herein allows the measurement system to be used in other inserts such as the hip, spine, ankle, and shoulder to name but a few. The measurement system can also be placed in the muscular-skeletal system or in a tool or equipment. The coupling of support structures 102 and 104 can utilize a variety of techniques such as mechanical, adhesives, and welding. The coupling of the structures can be temporary or permanent. In the intra-operative example, a strong adhesive holds the peripheral interior surfaces that align and mate together. The adhesive seals the internal cavity of insert 100 from an external environment. In one embodiment, the seal is hermetic such that solids, liquids and gasses cannot enter into the at least one interior cavity of insert 100. Separating support structures 102 and 104 can be a destructive process where support structures 102 and 104 can break or fracture rendering the device useless for the instance where it is a disposable device for a single application.

In one embodiment, at least one load-bearing surface of insert 100 comprises polycarbonate. The polycarbonate load-bearing surface can be articular surface 106, load-bearing surface 108, or both. The use of polycarbonate or other material having similar properties for support structures 102 and 104 is suitable for intra-operative measurements. In the example, support structures 102 and 104 both comprise polycarbonate. The use of polycarbonate provides the benefit of promoting wireless communication. Other joint components are often made of metal. The metal can act as a shield when insert 100 is placed in the joint thereby reducing the signal strength of the transmission. The use of a polymer such as polycarbonate is transmissive to the radio frequency signals being used by insert 100 for transmitting and receiving.

In general, articular surface 106 can flex to increase load coupling to the load plate. Allowing the articular surface to flex decouples load transfer through the periphery surface of support structure 102 that couples to support structure 204. Allowing articular surface 106 to flex directs the applied load to the load plate 112. More specifically, load plate 112 transfers and distributes the force, pressure, or load from the internal surface of support structure 102 to sensors 602 at predetermined locations. Sensors 602 are internal to the insert 100. The predetermined locations where sensors 602 are located correspond and relate to articular surface 106. Conversely, load-bearing surface 108 is a rigid surface that does not flex but has a large surface area for distributing load to a prosthetic component. In general, the load per unit area on load-bearing surface 108 is less than the load per unit area on articular surface 106. Moreover, the flexure of articular surface 106 ensures that loading thereon is directed principally to the load plate and not to the peripheral surface coupled to support structure 104. Correction or calibration can be used to further increase accuracy to take into account any applied articular load that is distributed through the peripheral surface of support structure 102 when compared to a reference. Allowing flexure of articular surface 106 and relying on load plate 112 for stiffness promotes a compact form factor.

A load applied to articular surface 106 is transferred through the flexible structure to an interior surface of support structure 102. The load plate 112 is coupled to the interior surface of support structure 102 for receiving the applied load. The load plate 112 is a rigid structure that does not flex. In one embodiment, load plate 112 comprises a metal such as steel or aluminum. The load plate 122 then distributes the loading to each sensor 602 proportionate to the location of the applied load to articular surface 106. The magnitude of the applied load to articular surface 106 can be calculated from the measured magnitudes of each sensor 602. The location of the load applied to articular surface 106 is calculated by knowing the positions of each sensor in relation to the articular surface 106 and the differential magnitudes between each sensor measurement.

In general, support structures 102 and 104 form an enclosure when coupled together for housing the measurement system that can include one or more sensor types that can measure different parameters of the muscular-skeletal system. The enclosure is sufficiently rigid to support loading applied by the joint without deflecting. Conversely, the articular surface 106 of support structure 102 can flex to support force, load, and pressure measurement.

Figure 9:
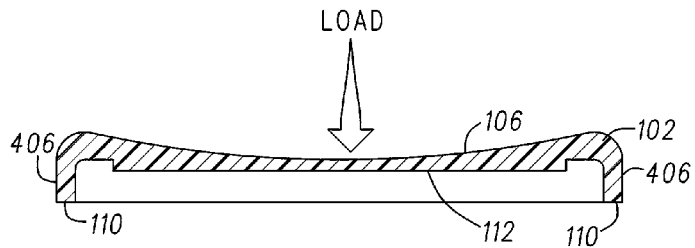
FIG. 9 illustrates a cross-sectional view of the support structure having a flexible articular surface in accordance with an example embodiment.

Referring briefly to FIG. 9, the articular surface 106 can flex under the loading. In one embodiment, the material of articular surface 106 is made sufficiently thin to allow flexing under loading applied by the muscular-skeletal system in the joint application. Support structure 102 includes a peripheral region 406 that couples to surface 110 of support structure 104. The flexible surface of articular 106 couples the applied load to the rigid load plate 112 while directing little or no loading through the peripheral region 406 of support structure 102 that couples to the surface 110 of support structure 104. In the example, support structure 102 comprises a polymer material such as polycarbonate. The interior surface underlying articular surface 106 couples to load plate 112. Other areas of support structure 102 do not flex substantially and can be rigid such that no flex occurs. Referring back to FIG. 8, the sensing assembly stack couples to the articular surface 106 and is supported by the load-bearing surface 108 of support structure 104. The load plate 112, pad regions 608, and interconnect 604 do not compress or compress slightly by the force, pressure, or load applied to articular surface 106. Load plate 112, pad regions 608, and interconnect 604 supports and transfers the force, pressure, or load to sensors 602. In the example, sensor 602 is a piezo-resistive film sensor that changes resistance as a function of loading applied thereto. In general, the change in thickness of the piezo-resistive film over the pressure measurement range required for an intra-operative load sensing application can be supported by flexing of articular surface 106 such that the load is applied to the load plate 112 and not other regions of support structure 102.

Figure 10:
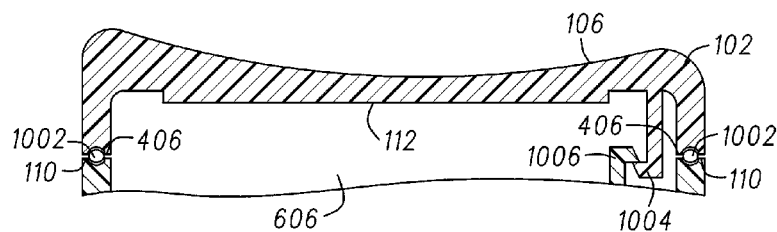
FIG. 10 illustrates a cross-sectional view of an insert with an inflexible articular surface having an elastic flexible seal in accordance with an example embodiment.

Referring to FIG. 10, an alternate structure and method for directing the load applied to articular surface 106 is illustrated. Support structure 102 includes a non-flexing articular surface 106. A flexible gasket 1002 is coupled to the peripheral surfaces of support structures 102 and 104. The flexible gasket 1002 couples between surfaces 406 and 110 respectively of support structures 102 and 104. Surfaces 406 and 110 can be shaped to retain flexible gasket 1002. For example, surfaces 406 and 110 can be concave to support a curved surface of flexible gasket 1002. Flexible gasket 1002 seals insert 100 thereby isolating the cavity 606 from an external environment. The support structures 102 and 104 are coupled together by a latch mechanism. The latch mechanism comprises a feature 1004 and a feature 1006 respectively extending from support structure 102 and support structure 104. Latch surfaces of features 1004 and 1006 interface and retain structures 102 and 104 when flexible gasket 1002 is compressed such that the features interlock together. Support structures 102 and 104 can respectively include more than one feature 1004 and 1006 for retaining the housing together. Flexible gasket 1002 comprises an elastic material that exerts an outward force on features 1004 and 1006 such that the retaining interface are forcibly held together. The flexible gasket 1002 can further flex or compress when a force is applied to articular surface 106 allowing the articular load to be applied to the sensor assembly stack for accurate measurement.

Figure 11:
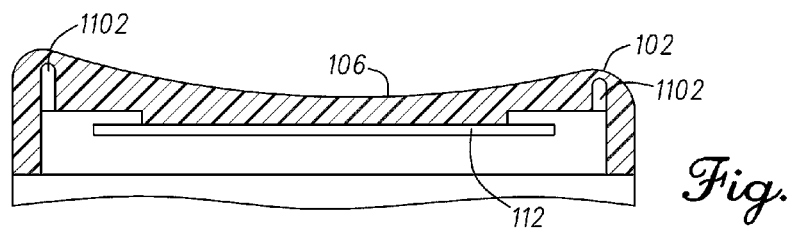
FIG. 11 illustrates a cross-sectional view of insert having a peripheral groove in the support structure having the articular surface in accordance with an example embodiment.

Referring to FIG. 11, an articular surface 106 modified to be flexible is provided. Similar to that described above, articular surface 106 is made flexible to direct loading to a load plate and to minimize load coupling through the surfaces 406 and 110 respectively of support structures 102 and 104. Surfaces 406 and 110 are coupled together at the periphery of insert 100. A groove 1102 is cut in the periphery of support structure 102. Groove 1102 allows articular surface 106 to flex when a load is applied. Articular surface 106 is rigid with little or no flexibility without groove 1102. In one embodiment, the groove is circumferential around the periphery of support structure 102. The groove 1102 is placed interior to the surfaces 406 and 110 within insert 100 thereby providing further decoupling.

Referring back to FIG. 8 a method of transferring a force, pressure, or load applied by the muscular-skeletal system is supported by the embodiment disclosed herein. The steps disclosed herein can be performed in any order or combination. In the method, a force, pressure, or load of the muscular-skeletal system is measured. An insert 100 is inserted in a joint of the muscular-skeletal system. The insert 100 has an articular surface 106 and a load-bearing surface 108. In a first step, the muscular-skeletal system applies a compressive force, pressure, or load to insert 100. In one embodiment, the measurement system is self-contained within insert 100, is substantially equal dimensionally to a passive final insert, measures load magnitude, and load position applied to articular surface 106. The articular surface 106 of support structure 102 allows movement of the joint of the muscular-skeletal system. In the example, the articular surface 106 interfaces with a prosthetic component coupled to a first bone. The support structure 104 has a load-bearing surface 108 that interfaces with a prosthetic component coupled to a second bone. The load-bearing surface 108 is retained to the second bone in a fixed relationship to support the distribution of loading thereto.

In a second step, the force, pressure, or load applied to the articular surface 106 is transferred from articular surface 106 to an interior surface of support structure 102. In general, the articular surface 106, and the interior surface comprise a common substrate of support structure 102. In a third step, the force, pressure, or load is coupled to sensors 602 housed within the cavity 606 of insert 100. The sensors 602 are at predetermined positions within insert 100 that correspond to locations on articular surface 106. The articular surface 106 flexes under loading to ensure transfer of the load to the sensors 602.

In a fourth step, flexing is achieved by forming the substrate or layer having the articular surface 106 and the interior surface having a thickness that allows flexing to direct the loading to the sensors 602 for measurement. The thickness can vary depending on the material used to form support structure 102 and the force, pressure, or load applied thereto. Alternatively, in a fifth step, flexing is achieved by forming the peripheral groove 1102 in support structure 102. In one embodiment, the peripheral groove 1102 is adjacent to a boundary of articular surface 106. For example, the peripheral groove 1102 is between the articular surface and the structural wall of support structure 102 having surface 406. The groove 1102 allows the articular surface 106 to flex under loading thereby directing the force, pressure, or load to the interior surface of support structure 102 and sensors 602.

In a sixth step, the electronic circuitry 618 for measuring the force, pressure, or load is housed in insert 100. At least one cavity 606 is formed internal to insert 100 when support structures 102 and 104 are coupled together. In a seventh step, the support structures 102 and 104 are sealed together such that the electronic circuitry 618 and sensors 602 are isolated from an external environment. In the example, surfaces 406 and 110 respectively of support structures 102 and 104 are coupled together by an adhesive. Surfaces 406 and 110 are attached and sealed around the entire periphery. The adhesive forms a bond to surfaces 406 and 110 that fractures or breaks support structures 102 and 104 during an attempt to separate.

In an eighth step, each sensor 602 is supported by a pad region 608 of support structure 104. The pad regions 608 are at predetermined locations corresponding to articular surface 106. Each pad region 608 couples to and is support by the load-bearing surface of support structure 104. In the example, at least a portion of the electronic circuitry 618 is housed between the sensors 602. In a ninth step, the sensors 602 are coupled to the articular surface through the load plate 112. The load plate couples to the interior surface of support structure 102. The support structure 104 includes at least one alignment feature 114. The alignment feature 114 aligns the load plate 112 to the interior surface of support structure 102.

The measurement system for measuring a parameter of the muscular-skeletal system disclosed herein is sterilized prior to being used intra-operatively or as an implant. The description of the sterilization process will refer to components illustrated in FIGS. 7 and 8. Insert 100 is a joint prosthetic component for the muscular-skeletal system having articular surface 106 and load-bearing surface 108. The articular surface 106 and load-bearing surface 108 are respectively major surfaces of support structures 102 and 104. The articular surface 106 interfaces with the muscular-skeletal system to support joint movement. Support structures 102 and 104 coupled together form an enclosure for a self-contained measurement system. The cavity 606 within insert 100 contains electronic circuitry 618 that is operatively coupled to at least one sensor 602. Support structures 102 and 104 are sealed together such that the cavity 606 is isolated from the external environment. The seal can be mechanical, a weld, or adhesives, which hold and seal structures 102 and 104 together. In one embodiment, structures 102 and 104 are coupled together to form a hermetic seal. In one embodiment, insert 100 is sterilized prior to use. The sterilization process sterilizes interior surfaces and exterior surfaces of insert 100. For example, articular surface 106, load-bearing surface 108, sidewall surfaces, and other exterior surfaces of insert 100 are sterilized. Similarly, the cavity 606 and the components comprising the measurement system are sterilized. The sterilization process comprises exposing the exterior and interior of insert 100 to a sterilization agent. In one process, insert 100 is exposed to a sterilization gas, sterilized, and packaged in a sterile container or package. The process takes place within a clean room environment. The container or packaging maintains sterility of insert 100 until it is used. Typically, the sterile container is opened immediately prior to use within the sterile field of an operating room thereby ensuring the sterile status of insert 100 before contact to a patient.

Figure 12:
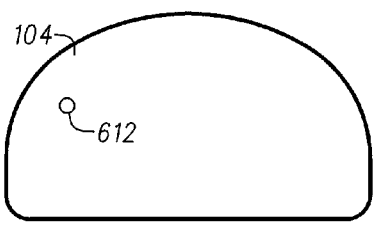
FIG. 12 illustrates the support structure having the load-bearing surface including the port for sterilization in accordance with an example embodiment.
Figure 13:
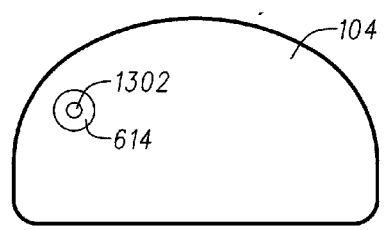
FIG. 13 illustrates a seal having a membrane overlying the port in accordance with an example embodiment.

Referring briefly to FIG. 12, the port 612 is shown in support structure 104. The port 612 couples the external environment to cavity 606 of insert 100. The sterilization gas enters into cavity 606 through the port 612. The components of FIGS. 6 and 7 can be referenced in the description of FIGS. 12-14. Seal 614 can include a membrane that is a barrier between the port and cavity 606. Seal 614 prevents the ingress of solids or liquids into the cavity 606. Referring briefly to FIG. 13, seal 614 is shown briefly coupled to an interior surface of support structure 104. Although not shown, one or more features on support structure 104 can retain an O-ring portion of seal 614 to the interior surface forming a seal. For example, the features can compress the ring portion of seal 614 to the interior surface of support structure 104 when support structures 102 and 104 are fastened together.

Figure 14:
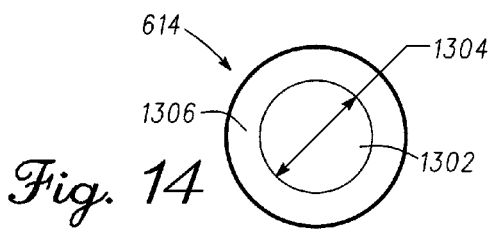
FIG. 14 illustrates the seal in accordance with an example embodiment.

FIG. 14 illustrates seal 614 in accordance with an example embodiment. In one embodiment, seal 614 is shaped as an o-ring with a gas permeable membrane 1302. A circumferential ring portion 1306 of seal 614 is compressed against the interior surface of support structure 104 adjacent to the port to seal the cavity housing the electronic circuitry from the ingress of liquid or solid matter from the external environment. Gas permeable membrane 1302 is located interior to ring portion 1306. Gas permeable membrane 1302 can be exposed to sterilization gas during the sterilization process. In one embodiment, membrane region 1302 can comprise silicone, which is a gas permeable material that prevents liquid or solid matter from entering into cavity 606 through port 612. Silicone is compliant, conformal, compressible, and elastic making it suitable for interfacing and sealing to a surface. Gas permeable membrane 1302 has a diameter 1304 that determines a rate of diffusion of the sterilization gas into the interior cavity 606. In one embodiment, the sterilization process is a timed event that sterilizes the interior and exterior surfaces of insert 100. The thickness and predetermined area of interior membrane region 1302 of seal 614 is selected to ensure that sufficient gas enters into cavity 606 for the time period of the sterilization process.

A method of providing intra-operative muscular-skeletal parameter measurement is supported by the embodiment disclosed hereinabove. The steps disclosed herein can be performed in any order or combination. In a first step, electronic circuitry 618 is housed within the insert 100. Insert 100 is a self-contained measurement system having electronic circuitry 618, sensors 602, and a power source 616 within a cavity 606. The cavity 606 is isolated from the external environment. In particular, insert 100 is sealed such that liquids and solids from the external environment cannot enter into cavity 606 to contaminate or affect the performance/reliability of the measurement system. Insert 100 has articular surface 106 and load-bearing surface 108 for interfacing with natural or prosthetic components of a joint. Articular surface 106 allows movement of a first bone in relation to a second bone. Insert 100 is substantially dimensionally equal to a final passive insert. In a second step, insert 100 is sterilized. The exterior surfaces and cavity 606 of insert 100 are sterilized.

In one embodiment, a sterilization process comprises exposing insert 100 to a sterilization gas. The sterilization gas kills biological contaminants that may be on insert 100 after manufacture and assembly. The insert 100 is exposed to a predetermined gas concentration for a predetermined length of time that ensures sterility. In a third step, the sterilizing gas couples through port 612 into cavity 606 for sterilizing interior regions and components within insert 100. In a fourth step, the insert includes a barrier to liquids and solids when assembled. The barrier prevents the liquids and solids from entering into the cavity 606 of insert 100. A seal 614 is placed between port 612 and cavity 606. The seal 614 covers and seals port 612. The seal 614 is permeable to gas but non-permeable to liquids and solids. After sterilization, insert 100 can be subjected to an evacuation process that removes or reduces the sterilization gas in or on the device. In a fifth step, insert 100 can be placed in a container or package that maintains sterility and prevents contamination prior to surgery.

Insert 100 can be used intra-operatively to provide quantitative measurements data on the muscular-skeletal system or implanted into the muscular-skeletal system to provide long-term or periodic measurements. In the intra-operative or implant example, the insert 100 is provided in the operating room to the surgical team. In a sixth step, the sterile packaging is opened within a sterile field of the operating room. In a seventh step, the insert 100 is removed from the packaging and inserted into a joint of the muscular-skeletal system. Insert 100 can be enabled for measurement prior to insertion or after the device is installed. In an eighth step, the enabled insert 100 measures a parameter of the muscular-skeletal system. In the example, the data measured by insert 100 is wirelessly sent to a receiving device. The receiving device can be equipment, tools, a processor, computer, digital logic, a display, a database, or other devices for using the parameter measurement data. In the operating room, the data can be continuously displayed allowing the surgical team to see the information over a range of joint motion or as modifications are being performed. In one embodiment, insert 100 when used intra-operatively is a low cost disposable measurement device. The low cost and ease of use promotes rapid adoption. Moreover, insert 100 provides the substantial benefit of providing quantitative data to supplement the subjective nature of orthopedic procedures done today. In a ninth step, insert 100 is disposed of after the surgery has been completed when used intra-operatively.

In an alternate embodiment, insert 100 does not have port 612 and seal 614. Insert 100 operates similarly as self-contained measurement system for measuring a parameter of the muscular-skeletal system as described hereinabove. Insert 100 has articular surface 106, load-bearing 108, and interior cavity 606 housing electronic circuitry 608. In general, the cavity 606 is not sterilized during the sterilization process before packaging. The cavity 606 is sealed and isolated from an external environment such that solids, liquids, and gases cannot enter or leave cavity 606. In one embodiment, the cavity 606 is hermetically sealed. The components comprising insert 100 are cleaned and assembled in a sterile environment such that contaminants are kept to a minimum. After assembly, the interior cavity 606 is no longer accessible. Subsequently, insert 100 undergoes an extensive sterilization process where the external surfaces are sterilized for use intra-operatively and as an implant. As disclosed above, the sterilization process can use a sterilization gas to sterilize all exposed regions of insert 100.

Insert 100 is assembled having the support structure 102 and the support structure 104. The support structures 102 and 104 houses electronic circuitry 618 and respectively having the articular surface 106 and the load-bearing surface 108. The support structures 102 and 104 can comprise in part a material such as polycarbonate, ultra high molecular weight polyethylene, metal, or other polymer materials. In the example, support structures 102 and 104 are molded polycarbonate structures. Sensors 602 are within insert 100 for measuring load magnitude and position of load on the articular surface 106. The electronic circuitry 618 is operatively coupled to sensors 602. A power source 616 within the insert 100 powers the electronic circuitry 618 during a measurement process. Support structures 102 and 104 respectively have peripheral surfaces 406 and 110 that are coupled together to form a sealed enclosure. The peripherals surfaces are sealed by adhesive, welding, elastic gasket, or other methods/devices for isolating the cavity 606 from allowing any solids, liquids, or gases from entering to the external environment after insert 100 is assembled. In particular, cavity 606 is sealed such that any chemicals or biological matter cannot pass to the external environment. As mentioned previously, insert 100 is subjected to a sterilization process that ensures sterility of the device for intra-operative and implant use. Insert 100 is placed in a sterile container or packaging until used in an operating room. The insert 100 used intra-operatively can be a disposable device that is disposed of as a biological hazardous material after the surgical procedure is completed. Power source 616 powers the device for a single use. The sealing process uses a strong adhesive to seal support structures 102 and 104 to prevent the insert 100 from being used a second time after disposal. Attempting to separate support structures 102 is likely a destructive process to insert 100 thereby acting as a deterrent for unauthorized reuse.

A method of providing intra-operative muscular-skeletal parameter measurement is supported by the embodiment disclosed hereinabove. Insert 100 has the articular surface 106 that interfaces with a natural or prosthetic surface coupled to the muscular-skeletal system for allowing movement of two bones in relation to one another. Sensors 602 within insert 100 couple to and measure the muscular-skeletal parameter when installed. The steps disclosed herein can be performed in any order or combination. In a first step, electronic circuitry 618 is housed within the insert 100. Insert 100 is a self-contained measurement system having electronic circuitry 618, sensors 602, and a power source 616 within a cavity 606. In a second step, cavity 606 is sealed and isolated from an external environment. In a third step, a sterilization process sterilizes the exposed or external surfaces of insert 100. Assembly of insert 100 occurs before the sterilization process. For example, one sterilization process comprises insert 100 being exposed to a sterilization gas for a predetermined time period. In the method, the cavity 606 is not sterilized during the sterilization process. Sterility is maintained by sealing the cavity 606 during assembly such that solids, liquids, or gases cannot pass through the seal. The sterilization gas does not penetrate within cavity 606. In general, the components and assembly process are tightly controlled to minimize or eliminate contaminants in cavity 606.

In a fourth step, the insert 100 is placed in a sterile container or sterile packaging after the sterilization process. The packaging maintains the sterility of the external or exposed surfaces of insert 100 until it is used as an intra-operative prosthetic component or as an implanted prosthetic component. In a fifth step, the sterile packaging is opened in a sterile environment prior to use. In one embodiment, the sterile packaging is opened within the sterile field of the operating room thereby minimizing a possibility of contamination of insert 100. In a sixth step, the insert 100 is inserted into a joint of the muscular-skeletal system. The insert 100 allows a natural range of motion of the joint such that the bones of the joint move in relation to one another. In a seventh step, insert 100 measures one or more parameters of the muscular-skeletal system. The measurements can occur over the range of motion and provide real-time data as adjustments are made to the joint. In an eighth step, the insert 100 is disposed of after surgery. The insert 100 is a disposable item for use in a single application. Typically, insert 100 is disposed of as hazardous waste due to contact with biological matter.

In one embodiment, the enclosure of insert 100 for measuring a parameter of the muscular-skeletal system comprises a polymer material. In one embodiment, at least one of the load-bearing surfaces of insert 100 comprises polycarbonate. Polycarbonate is a lightweight material that is biocompatible having sufficient structural strength to support joint loading. In particular, polycarbonate is used in insert 100 for intra-operative measurements to aid in the installation of a permanent or final joint prosthetic system. The use of polycarbonate provides the further benefit of being easily formed in complex shapes, low cost for disposable applications, sterilizable, and transmissive to radio frequency signals for short distance communications required for providing real-time intra-operative quantitative data.

Referring to FIGS. 7 and 8, insert 100 comprises the support structure 102 having the articular surface 106 and the support structure 104 having the load bearing surface 108. The support structures 102 and 104 have alignment features that align the housing together during assembly. Peripheral surfaces 110 and 406 interface or mate together when aligned and structures 102 and 104 are coupled together to form. The peripheral surfaces 110 and 406 are sealed together such that the cavity 606 encloses the self-contained measurement system for measuring a parameter of the muscular-skeletal system. The peripheral surfaces 110 and 106 are sealed by adhesive, welding, elastic seal, or other method to isolate the cavity 606 and the measurement system from the external environment. In one embodiment, the insert 100 measures load and position of load. The cavity 606 houses, electronic circuitry 618, load sensors 602, and a power source 616. Support structures 102 and 104 can include shims to change the height during the surgery. The insert 100 including the measurement system is substantially dimensionally equal to the final insert placed in the joint.

In one embodiment, the support structures 102 and 104 are formed of polycarbonate. Support structures 102 and 104 can be molded for repeatable construction and low cost. The molding process can include injection molding, thermoforming, vacuum forming, and mold processes. The support structures can also be machined from a solid block of material. In one embodiment, the articular surface 106 is flexible under loading by the joint during an installation process. The polycarbonate layer comprising articular surface 106 can be made thin to allow flexing as disclosed above. A peripheral groove can also be cut in support structure 102 to allow a thicker polycarbonate layer comprising articular surface 106 to flex under loading. The thicker polycarbonate layer comprising load-bearing surface 108 is rigid and does not flex whereby the peripheral groove allows flexing. In one embodiment, alignment features 114 and 410 are formed in structures 102 and 104 of polycarbonate during the mold process. The support structure 104 further includes pad regions 608 at predetermined locations comprising polycarbonate for supporting sensors 602. The position of pad regions 608 corresponds to locations on articular surface 106. The positions are used in the calculations to identify where the load magnitude and the position where the load is applied to the articular surface 106. For brevity, it should be noted that insert 100 comprising support structures 102 and 104 can similarly be formed of ultra-high molecular weight polyethylene as disclosed hereinabove.

Figure 15:
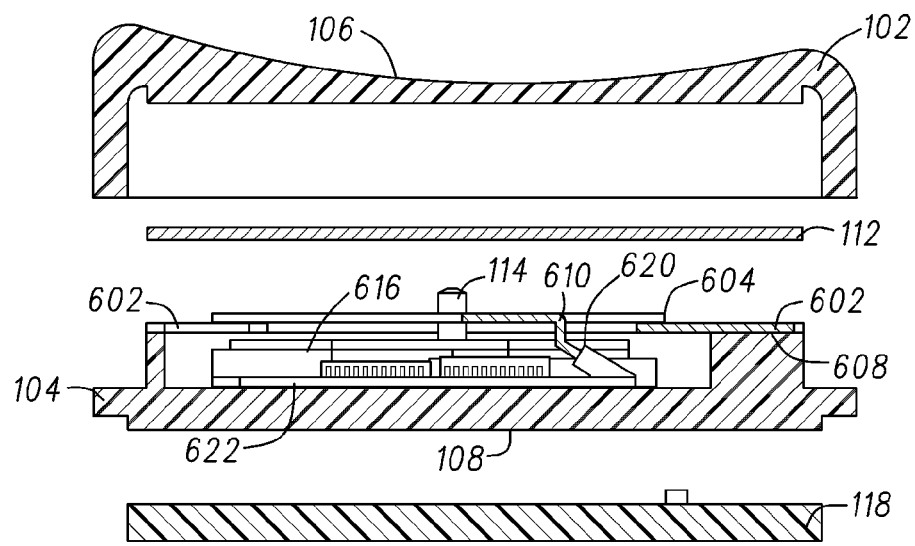
FIG. 15 illustrates the planar interconnect coupling to the sensors in accordance with an example embodiment.

FIG. 15 illustrates a cross-sectional view of planar interconnect 604 coupling to sensors 602 in accordance with an example embodiment. Sensors 602 are located at each vertex of a triangular area of support structure 104. Sensors 602 are supported by pad regions 608 coupled to the load-bearing surface 108. Electronic circuitry 618 at least partially underlies planar interconnect 604 in cavity 606 of support structure 104. Planar interconnect 604 is aligned to support structure 104 and more specifically to sensors 602 by alignment features 114. The planar interconnect 604 aligns such that terminals on sensors 602 couple to interconnect on planar interconnect 604. In the example, the sensors 602 are film sensors such as piezo-resistive film sensors having electrical contact regions that correspond to electrical contact regions on planar interconnect 604. The planar interconnect 602 can be physically and electrically coupled to sensors 602 by solder or conductive epoxy. In one embodiment, a spacing exists between planar interconnect 604 and the electronic components 618. The space ensures that planar interconnect 604 does not contact electronic components 618 when a loading is applied to insert 100.

In the illustration, electronic circuitry 618 is mounted on a printed circuit board 622. The printed circuit board 622 can further include an integrated antenna, power source 616, and connector 620. The planar interconnect 604 has a flexible tab 610 that extends to and is aligned with connector 620. In the example, flexible tab 610 has multiple connection points that couple to connection points on connector 620. In one embodiment, the flexible tab 610 is inserted in connector 620 and a clamp of connector 620 retains the flexible tab 610 and applies pressure to each connection to ensure a reliable electrical connection. The power source 616, electronic circuitry 618 and sensors 602 are coupled by printed circuit board 622 and planar interconnect 604 to form the self-contained measurement system. In an alternate embodiment, planar interconnect 604 can couple to one or more electronic components. For example, planar interconnect 604 can have connection points for coupling to the power source 616 or other connection points that underlie planar interconnect 604.

The load plate 112 is illustrated overlying planar interconnect 604. The load plate 112 is aligned by alignment features 114 of support structure 104 to sensors 602. The load plate includes openings that receive alignment features 114 therethrough. A portion of load plate 112 overlies each sensor 602. In particular, load plate 112 is triangular in shape and each vertex of load plate 112 overlies a corresponding sensor 602.

The load plate 112 distributes a force, pressure, or load applied to articular surface 106 of support structure 102 to sensors 602. In the embodiment, the load plate is triangular in shape.

Figure 16:
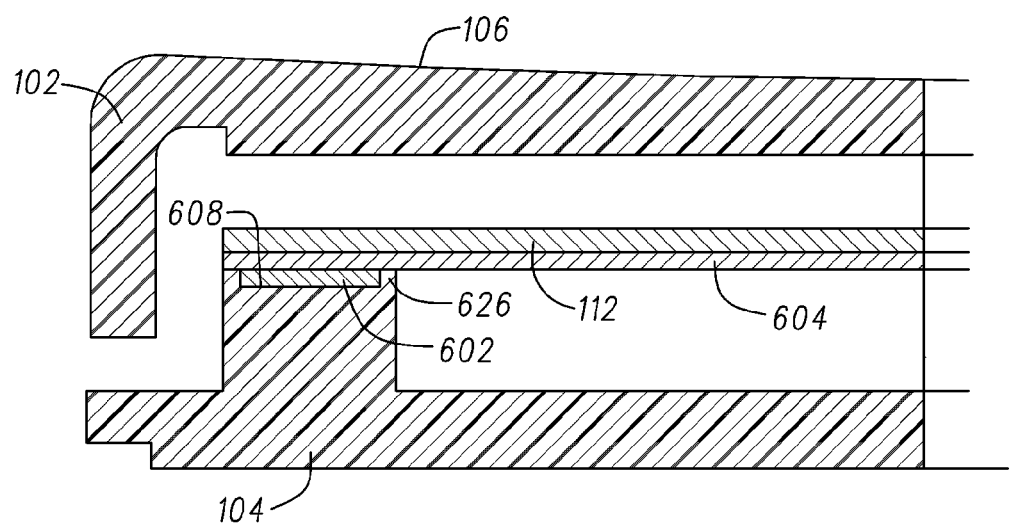
FIG. 16 illustrates a partial cross-sectional view of a sensor assembly in accordance with an example embodiment.

FIG. 16 illustrates a cross-sectional view of a sensor assembly in accordance with an example embodiment. The sensor assembly comprises the pad region 608, planar interconnect 604, sensor 602, and load plate 112. In one embodiment, sensor 602 is located on pad region 608. The sensor 602 can be positioned and retained by one or more retaining features. A portion of planar interconnect 604 is placed on sensor 602 such that electrical connection points between sensor 602 and planar 604 interface. Planar interconnect 604 comprises a non-compressible material that transfers a force, pressure, or load to sensor 602. The load plate 112 is placed on planar interconnect 604 to couple the force, pressure, or load to sensor 602. The load plate 112 comprises a rigid material or metal. In one embodiment, load plate 112 is formed from steel. The load plate 112 has a surface that is co-planar to a surface of planar interconnect 604. The sensing assembly can be assembled by a process of stacking components.

Figure 17:
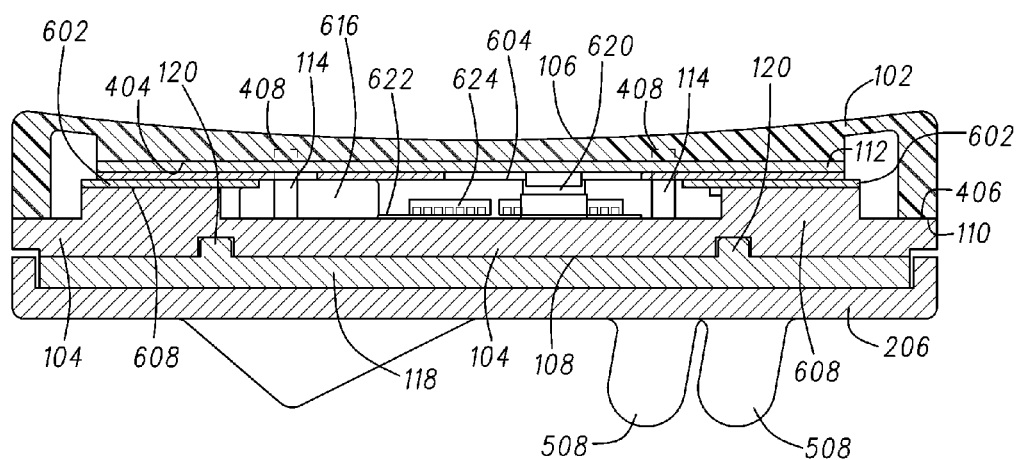
FIG. 17 illustrates a cross-sectional view of the assembled insert in accordance with an example embodiment.

FIG. 17 illustrates a cross-sectional view of assembled insert 100 in accordance with an example embodiment. Insert 100 comprises support structure 102 coupled to support structure 104 whereby the interior of the self-contained measurement system is isolated from the external environment. Support structures 102 and 104 respectively have the articular surface 106 and load-bearing surface 108 for coupling to shim 118 or one or more joint prosthetic components. A shim 118 can be used to change height and couple to a prosthetic component. Insert 100 inserted in the joint allows articulation of one bone in relation to another bone.

Insert 100 measures a parameter of the muscular-skeletal system. In one embodiment, three sensors measure a force, pressure, or load magnitude applied to the articular surface 106 when the insert 100 is inserted between other installed prosthetic components. Each sensor couples to a predetermined area of articular surface 106. The load-bearing surface 108 supports each sensor. Measurement of the load magnitude applied to articular surface 106 and position of load on articular surface 106 can be calculated from the sensor measurements.

Alignment features 114 are shown extending from support structure 104. Alignment features 114 couple through openings in planar interconnect 604, load plate 112, and into openings 408 of support structure 102. Alignment features 114 align interconnect 604 and load plate 112 to support structure 104 and more particularly to pad regions 608 and sensors 602. Planar interconnect 604 overlies and electrically couples to terminals of sensors 602. Planar interconnect 604 couples the three sensors 602 to electronic circuitry 618. Load plate 112 can have a surface that is co-planar to the surface of planar interconnect 604. As mentioned previously, load plate 112 may be triangular in shape and is supported at each vertex by sensors 602 and pad regions 608. Electronic circuitry 618 is shown in the cavity underlying the planar interconnect 604 and load plate 112. The planar interconnect 604 is spaced from electronic circuitry 618 to prevent contact under all loading conditions. In general, piezo-resistive film sensors used as sensors 602 to measure force, pressure, or load do not compress significantly over the expected load range for intra-operative installation measurements.

The support structure 102 includes interior surface 404 that couples to load plate 112. Interior surface 404 of support structure 102 is co-planar to the surface of the load plate 112. In one embodiment, support structure 102 can be formed, molded, or machined from a polymer material such as polycarbonate or ultra high molecular weight polyethylene having articular surface 106 and interior surface 404. The layer of polymer material between articular surface 106 and interior surface 404 of support structure 102 can flex but does not compress substantially under loading. Interior surface 404 of support structure 102 has openings 408 for receiving alignment features 114. Alignment features 114 align support structure 104 to support structure 102. Peripheral regions 110 and 406 respectively of support structure 104 and support structure 102 are coupled to seal or isolate the measurement system from the external environment. Welding or an adhesive can be used to form the seal between peripheral regions 110 and 406.

A method of assembling a self-contained measurement system within a prosthetic component is supported by the embodiment disclosed hereinabove. In general, the assembly method provides a high performance, small form factor, reliable, and sterile measurement system suitable for prosthetic components, tools, and equipment. In a first step, the electronic circuitry 618 is inserted into the cavity 606 of support structure 104. The electronic circuitry 618 can be mounted on a printed circuit board 622. Printed circuit board 622 can be supported and retained by one or more features formed in support structure 104. Pad regions 608 are at the vertices of a triangle. Pad regions 608 are supported by and couple to load-bearing surface 108. In a second step, sensors 602 are placed on the pad regions 608 of support structure 104. The pad regions 608 can have alignment and retaining features for holding sensors 602 in a predetermined position. In one embodiment, the sensors 602 are piezo-resistive film sensors having a low profile. In the example, a portion of sensors 602 can extend over the electronic circuitry 618 but do not make physical contact thereto. In a third step, an interconnect 604 is aligned to sensors 602 by alignment features 114. The alignment features 114 are formed in support structure 104. In particular, alignment features 114 couple through slots or openings in interconnect 604. In one embodiment, interconnect 604 is planar and partially overlies sensors 602 and cavity 606. The planar shape of interconnect 604 overlies but does not physically contact electronic circuitry 618. Interconnect 604 has conductive regions that align with and couple to corresponding conductive regions on sensors 602. In a fourth step, interconnect 604 can be coupled by solder, conductive epoxy, a compressive force, and other known methods to make appropriate electrical connection to the terminals of sensors 602.

The printed circuit board 622 can include a connector. The connector can have multiple connection points and a retention mechanism. The connector couples to electronic circuitry 618 of the measurement system. The interconnect 604 can include a tab that extends from interconnect 604. The tab is flexible. In a fifth step, the tab is inserted into the connector. The connector can have a clamping mechanism or other retaining device to hold the connection points on the tab of interconnect 604 coupled with connection points on the connector. The clamping mechanism forcibly retains the tab in the connector to prevent decoupling and maintain electrical contact during use. In a seventh step, load plate 112 couples to alignment features 114 of support structure 104. The alignment features 114 align the load plate 112 to the sensors 602. In an eighth step, the load plate 112 overlies sensors 602. Under loading, the load plate 112 couples and distributes a force, pressure, or load to each sensor corresponding to the location of an applied force, pressure, or load to the articular surface 106. In a ninth step, the support structure 102 having the articular surface 106 is aligned to the support structure 104. In the example, alignment is achieved by alignment features 114 coupling to alignment features 410 in support structure 102. In the example, alignment features 410 are openings in the interior surface of support structure 102. Support structures 102 and 104 are coupled together such that the interior surface of support structure 102 couples to load plate 112. Support structures 102 and 104 are sealed together thereby forming an enclosure surrounding electronic circuitry 618 and sensors 602 that is isolated from the external environment.

Figure 18:
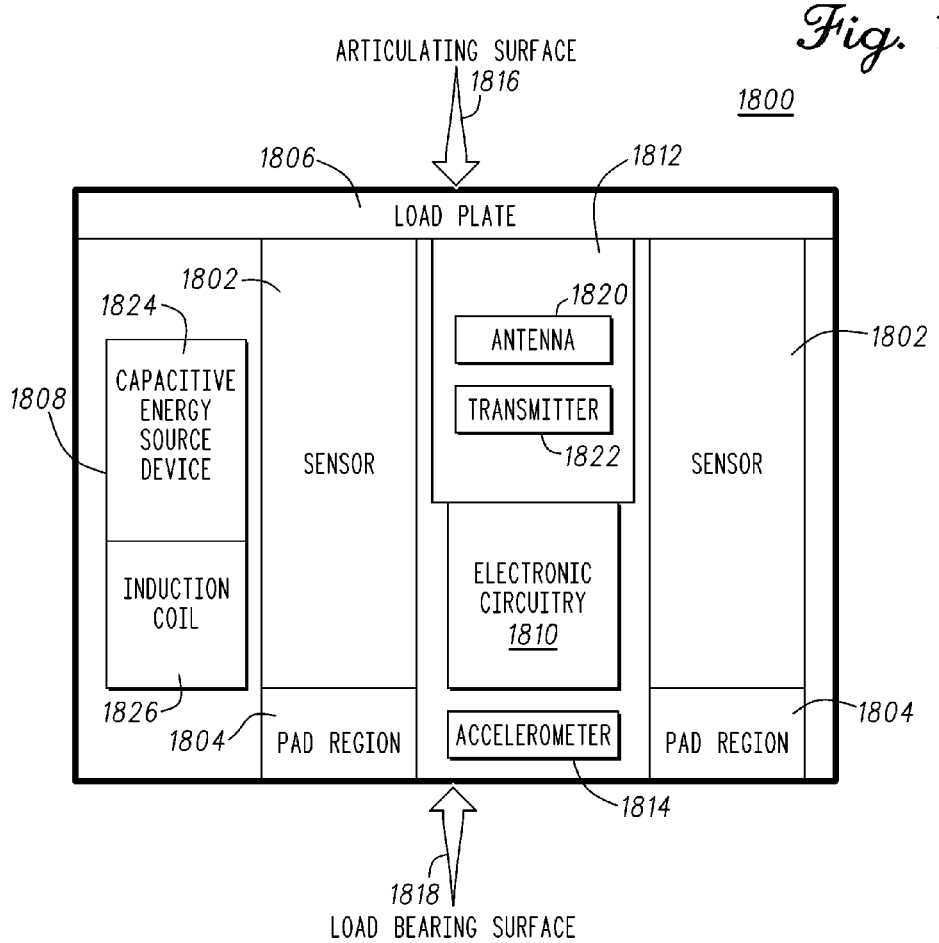
FIG. 18 illustrates a block diagram of the components of an insert in accordance with an example embodiment.

FIG. 18 illustrates a block diagram of the components of an insert 1800 in accordance with an example embodiment. It should be noted that insert 1800 could comprise more or less than the number of components shown. In one embodiment, insert 1800 is a prosthetic component allowing parameter measurement and articulation of the muscular-skeletal system. As illustrated, the insert 1800 includes one or more sensors 1802, pad regions 1804, a load plate 1806, a power source 1808, electronic circuitry 1810, a transceiver 1812, and an accelerometer 1814. In a non-limiting example, the insert 1800 can measure an applied compressive force.

The sensors 1802 can be positioned, engaged, attached, or affixed to the contact surfaces 1816 and 1818. In at least one example embodiment, contact surfaces 1816 and 1818 are load-bearing surfaces. In the example of a knee insert, surface 1816 is a load-bearing articular surface that contacts a natural or prosthetic femoral condyle to allow movement of a knee joint. Contact surface 1818 is a load-bearing surface. In the example, contact surface 1818 contacts a tibial surface or a tibial prosthetic component in a fixed position. Surfaces 1816 and 1818 can move and tilt with changes in applied load actions, which can be transferred to the sensors 1802 and measured by the electronic circuitry 1810. The electronic circuitry 1810 measures physical changes in the sensors 1802 to determine parameters of interest, for example a level, distribution and direction of forces acting on the contact surfaces 1816 and 1818. The insert 1800 is powered by an internal power source 1808.

The architecture allows different types of sensors to be used to measure a force, pressure, or load. Sensor types such as piezo-resistive sensors, mems devices, strain gauges, and mechanical sensors can overlie pad regions 1804 to generate signals related to a compressive force applied to surface 1816. As one example, sensors 1802 can comprise an elastic or compressible propagation structure between a first transducer and a second transducer. The transducers can be an ultrasound (or ultrasonic) resonator while the elastic or compressible propagation structure acts as an ultrasound waveguide. The electronic circuitry 1810 is electrically coupled to the transducers to translate changes in the length (or compression or extension) of the compressible propagation structure to parameters of interest, such as force. The system measures a change in the length of the compressible propagation structure (e.g., waveguide) responsive to an applied force and converts this change into electrical signals, which can be transmitted via the transceiver 1812 to convey a level, direction, or location of the applied force. For example, the compressible propagation structure has known and repeatable characteristics of the applied force versus the length of the waveguide. Precise measurement of the length of the waveguide using ultrasonic signals can be converted to a force using the known characteristics. In yet other arrangements, the sensors can include piezoelectric, pH, motion, capacitive, optical or temperature sensors to provide other parameter measurements of the muscular-skeletal system.

In one embodiment, electronic circuitry 1810 comprises an application specific integrated circuit (ASIC). The architecture of the ASIC supports performance, power consumption, and form factor specifications required for a self contained intra-operative and implant measurement prosthetic component. In particular, electronic circuitry 1810 includes multiple inputs, outputs, and input/outputs thereby allowing both serial and parallel measurement and data transfer. The ASIC also incorporates digital control logic to manage control functions of insert 1800. The electronic circuitry 1810 or ASIC incorporates A/D and D/A circuitry (not shown) to digitize current and voltage output from different types of sensing components.

The accelerometer 1814 can measure acceleration and static gravitational pull. Accelerometer 1814 can be single-axis and multi-axis accelerometer structures that detect magnitude and direction of the acceleration as a vector quantity. Accelerometer 1814 can also be used to sense orientation, vibration, impact and shock. The electronic circuitry 1810 in conjunction with the accelerometer 1814 and sensors 1802 can measure parameters of interest (e.g., distributions of load, force, pressure, displacement, movement, rotation, torque and acceleration) relative to orientations of insert 1800 with respect to a reference point. In such an arrangement, spatial distributions of the measured parameters relative to a chosen frame of reference can be computed and presented for real-time display.

The transceiver 1812 comprises a transmitter 1822 and an antenna 1820 to permit wireless operation and telemetry functions. In various embodiments, the antenna 1820 can be configured by design as an integrated loop antenna. The integrated loop antenna is configured at various layers and locations on a printed circuit board having other intercoupled electrical components. Once initiated the transceiver 1812 can broadcast the parameters of interest in real-time. The telemetry data can be received and decoded with various receivers, or with a custom receiver. The wireless operation can eliminate distortion of, or limitations on, measurements caused by the potential for physical interference by, or limitations imposed by, wiring and cables coupling the sensing module with a power source or with associated data collection, storage, display equipment, and data processing equipment.

The transceiver 1812 receives power from the power source 1808 and can operate at low power over various radio frequencies by way of efficient power management schemes, for example, incorporated within the electronic circuitry 1810. As one example, the transceiver 1812 can transmit data at selected frequencies in a chosen mode of emission by way of the antenna 1820. The selected frequencies can include, but are not limited to, ISM bands recognized in International Telecommunication Union regions 1, 2 and 3. A chosen mode of emission can be, but is not limited to, Gaussian Frequency Shift Keying, (GFSK), Amplitude Shift Keying (ASK), Phase Shift Keying (PSK), Minimum Shift Keying (MSK), Frequency Modulation (FM), Amplitude Modulation (AM), or other versions of frequency or amplitude modulation (e.g., binary, coherent, quadrature, etc.).

The antenna 1820 can be integrated with components of the sensing module to provide the radio frequency transmission. The antenna 1820 and coupling of electronic circuitry 1810 can be integrated into a printed circuit board. The antenna 1820 can further include a matching network for efficient transfer of the signal. This level of integration of the antenna and electronics enables reductions in the size and cost of wireless equipment. Potential applications may include, but are not limited to any type of short-range handheld, wearable, or other portable communication equipment where compact antennas are commonly used. This includes disposable modules or devices as well as reusable modules or devices and modules or devices for long-term use.

The power source 1808 provides power to electronic components of the insert 1800. In one embodiment, the power source 1808 can be charged by wired energy transfer, short-distance wireless energy transfer or a combination thereof. External power sources for providing wireless energy to power source 1808 can include, but are not limited to, a battery or batteries, an alternating current power supply, a radio frequency receiver, an electromagnetic induction coil, energy harvesting, magnetic resonance a photoelectric cell or cells, a thermocouple or thermocouples, or an ultrasound transducer or transducers. By way of power source 1808, insert 1800 can be operated with a single charge until the internal energy is drained. It can be recharged periodically to enable continuous operation. The power source 1808 can further utilize power management techniques for efficiently supplying and providing energy to the components of insert 1800 to facilitate measurement and wireless operation. Power management circuitry can be incorporated on the ASIC to manage both the ASIC power consumption as well as other components of the system.

The power source 1808 minimizes additional sources of energy radiation required to power the sensing module during measurement operations. In one embodiment, as illustrated, the energy storage 1808 can include a capacitive energy storage device 1824 and an induction coil 1826. The external source of charging power can be coupled wirelessly to the capacitive energy storage device 1824 through the electromagnetic induction coil or coils 1826 by way of inductive charging. The charging operation can be controlled by power management systems designed into, or with, the electronic circuitry 1810. For example, during operation of electronic circuitry 1810, power can be transferred from capacitive energy storage device 1810 by way of efficient step-up and step-down voltage conversion circuitry. This conserves operating power of circuit blocks at a minimum voltage level to support the required level of performance. An alternative to the capacitive energy storage device 1824 is a rechargeable battery disclosed hereinabove that could be recharged wirelessly as described herein.

In one configuration, the external power source can further serve to communicate downlink data to the transceiver 1812 during a recharging operation. For instance, downlink control data can be modulated onto the wireless energy source signal and thereafter demodulated from the induction coil 1826 by way of electronic circuitry 1810. This can serve as a more efficient way for receiving downlink data instead of configuring the transceiver 1812 for both uplink and downlink operation. As one example, downlink data can include updated control parameters that the insert 1800 uses when making a measurement, such as external positional information, or for recalibration purposes. It can also be used to download a serial number or other identification data.

The electronic circuitry 1810 manages and controls various operations of the components of the sensing module, such as sensing, power management, telemetry, and acceleration sensing. It can include analog circuits, digital circuits, integrated circuits, discrete components, or any combination thereof. In one arrangement, it can be partitioned among integrated circuits and discrete components to minimize power consumption without compromising performance. Partitioning functions between digital and analog circuit enhances design flexibility and facilitates minimizing power consumption without sacrificing functionality or performance. Accordingly, the electronic circuitry 1810 can comprise one or more integrated circuits or ASICs, for example, specific to a core signal-processing algorithm.

In another arrangement, the electronic circuitry 1810 can comprise a controller such as a programmable processor, a Digital Signal Processor (DSP), a microcontroller, or a microprocessor, with associated storage memory and logic. The controller can utilize computing technologies with associated storage memory such a Flash, ROM, RAM, SRAM, DRAM or other like technologies for controlling operations of the aforementioned components of the sensing module. In one arrangement, the storage memory may store one or more sets of instructions (e.g., software) embodying any one or more of the methodologies or functions described herein. The instructions may also reside, completely or at least partially, within other memory, and/or a processor during execution thereof by another processor or computer system.

The electronics assemblage also supports testability and calibration features that assure the quality, accuracy, and reliability of the completed wireless sensing module or device. A temporary bi-directional interconnect assures a high level of electrical observability and controllability of the electronics. The test interconnect also provides a high level of electrical observability of the sensing subsystem, including the transducers, waveguides, and mechanical spring or elastic assembly. Carriers or fixtures emulate the final enclosure of the completed wireless sensing module or device during manufacturing processing thus enabling capture of accurate calibration data for the calibrated parameters of the finished wireless sensing module or device. These calibration parameters are stored within the on-board memory integrated into the electronics assemblage.

Applications for the electronic assembly comprising the sensors 1802 and electronic circuitry 1810 may include, but are not limited to, disposable modules or devices as well as reusable modules or devices and modules or devices for long-term use. In addition to non-medical applications, examples of a wide range of potential medical applications may include, but are not limited to, implantable devices, modules within implantable devices, intra-operative implants or modules within intra-operative implants or trial inserts, modules within inserted or ingested devices, modules within wearable devices, modules within handheld devices, modules within instruments, appliances, equipment, or accessories of all of these, or disposables within implants, trial inserts, inserted or ingested devices, wearable devices, handheld devices, instruments, appliances, equipment, or accessories to these devices, instruments, appliances, or equipment.

Figure 19:
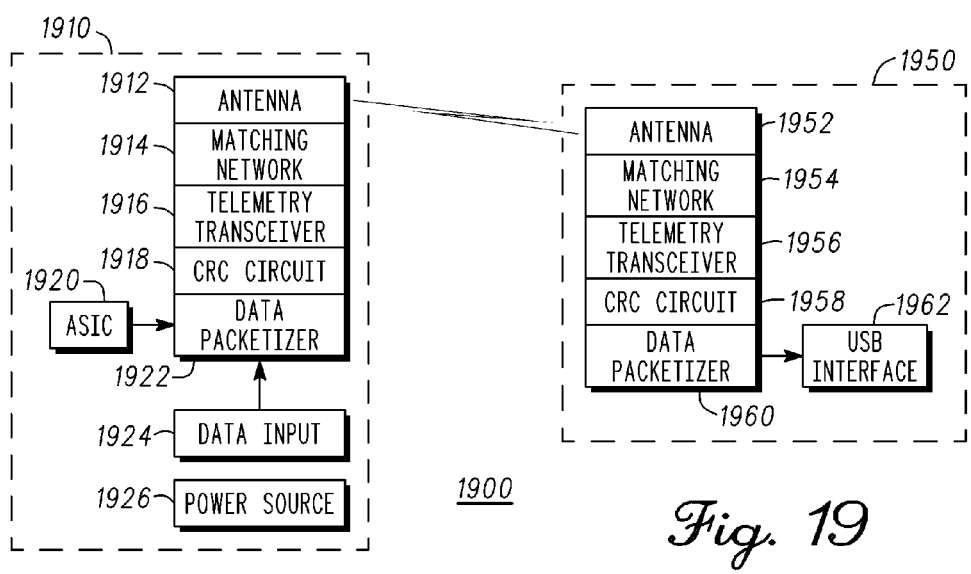
FIG. 19 illustrates communications system 1900 for short-range telemetry in accordance with an example embodiment.

FIG. 19 illustrates a communications system 1900 for short-range telemetry in accordance with an example embodiment. As illustrated, the communications system 1900 comprises medical device communications components 1910 in a prosthetic component and receiving system communications in a processor based system. In one embodiment, the receiving system communications are in or coupled to a computer or laptop computer that is external to the sterile field of the operating room. The surgeon can view the laptop screen or a display coupled to the computer while performing surgery. The medical device communications components 1910 are operatively coupled to include, but not limited to, the antenna 1912, a matching network 1914, the telemetry transceiver 1916, a CRC circuit 1918, a data packetizer 1922, a data input 1924, a power source 1926, and an application specific integrated circuit (ASIC) 1920. The medical device communications components 1910 may include more or less than the number of components shown and are not limited to those shown or the order of the components.

The receiving station communications components comprise an antenna 1952, a matching network 1954, the telemetry transceiver 1956, the CRC circuit 1958, the data packetizer 1960, and optionally a USB interface 1962. Notably, other interface systems can be directly coupled to the data packetizer 1960 for processing and rendering sensor data.

In general, the electronic circuitry is operatively coupled to one or more sensors of the prosthetic component. In one embodiment, the data generated by the one or more sensors can comprise a voltage or current value from a mems structure, piezo-resistive sensor, strain gauge, mechanical sensor or other sensor type that is used to measure a parameter of the muscular-skeletal system. The data packetizer 1922 assembles the sensor data into packets; this includes sensor information received or processed by ASIC 1920. The ASIC 1920 can comprise specific modules for efficiently performing core signal processing functions of the medical device communications components 1910. The ASIC 1920 provides the further benefit of reducing the form factor of insert sensing device to meet dimensional requirements for integration into temporary or permanent prosthetic components.

The CRC circuit 1918 applies error code detection on the packet data. The cyclic redundancy check is based on an algorithm that computes a checksum for a data stream or packet of any length. These checksums can be used to detect interference or accidental alteration of data during transmission. Cyclic redundancy checks are especially good at detecting errors caused by electrical noise and therefore enable robust protection against improper processing of corrupted data in environments having high levels of electromagnetic activity. The telemetry transceiver 1916 then transmits the CRC encoded data packet through the matching network 1914 by way of the antenna 1912. The matching networks 1914 and 1954 provide an impedance match for achieving optimal communication power efficiency.

The receiving system communications components 1950 receive transmission sent by medical device communications components 1910. In one embodiment, telemetry transceiver 1916 is operated in conjunction with a dedicated telemetry transceiver 1956 that is constrained to receive a data stream broadcast on the specified frequencies in the specified mode of emission. The telemetry transceiver 1956 by way of the receiving station antenna 1952 detects incoming transmissions at the specified frequencies. The antenna 1952 can be a directional antenna that is directed to a directional antenna of components 1910. Using at least one directional antenna can reduce data corruption while increasing data security by further limiting where the data is radiated. A matching network 1954 couples to antenna 1952 to provide an impedance match that efficiently transfers the signal from antenna 1952 to telemetry receiver 1956. Telemetry receiver 1956 can reduce a carrier frequency in one or more steps and strip off the information or data sent by components 1910. Telemetry receiver 1956 couples to CRC circuit 1958. CRC circuit 1958 verifies the cyclic redundancy checksum for individual packets of data. CRC circuit 1958 is coupled to data packetizer 1960. Data packetizer 1960 processes the individual packets of data. In general, the data that is verified by the CRC circuit 1958 is decoded (e.g., unpacked) and forwarded to an external data processing device, such as an external computer, for subsequent processing, display, or storage or some combination of these.

The telemetry transceiver 1956 is designed and constructed to operate on very low power such as, but not limited to, the power available from the powered USB port 1962, or a battery. In another embodiment, the telemetry transceiver 1956 is designed for use with a minimum of controllable functions to limit opportunities for inadvertent corruption or malicious tampering with received data. The telemetry transceiver 1956 can be designed and constructed to be compact, inexpensive, and easily manufactured with standard manufacturing processes while assuring consistently high levels of quality and reliability.

In one configuration, the communication system 1900 operates in a transmit-only operation with a broadcasting range on the order of a few meters to provide high security and protection against any form of unauthorized or accidental query. The transmission range can be controlled by the transmitted signal strength, antenna selection, or a combination of both. A high repetition rate of transmission can be used in conjunction with the Cyclic Redundancy Check (CRC) bits embedded in the transmitted packets of data during data capture operations thereby enabling the receiving system to discard corrupted data without materially affecting display of data or integrity of visual representation of data, including but not limited to measurements of load, force, pressure, displacement, flexion, attitude, and position within operating or static physical systems.

By limiting the operating range to distances on the order of a few meters, the telemetry transceiver 1916 can be operated at very low power in the appropriate emission mode or modes for the chosen operating frequencies without compromising the repetition rate of the transmission of data. This mode of operation also supports operation with compact antennas, such as an integrated loop antenna. The combination of low power and compact antennas enables the construction of, but is not limited to, highly compact telemetry transmitters that can be used for a wide range of non-medical and medical applications.

The transmitter security as well as integrity of the transmitted data is assured by operating the telemetry system within predetermined conditions. The security of the transmitter cannot be compromised because it is operated in a transmit-only mode and there is no pathway to hack into medical device communications components. The integrity of the data is assured with the use of the CRC algorithm and the repetition rate of the measurements. The limited broadcast range of the device minimizes the risk of unauthorized reception of the data. Even if unauthorized reception of the data packets should occur, there are counter measures in place that further mitigate data access. A first measure is that the transmitted data packets contain only binary bits from a counter along with the CRC bits. A second measure is that no data is available or required to interpret the significance of the binary value broadcast at any time. A third measure that can be implemented is that no patient or device identification data is broadcast at any time.

The telemetry transceiver 1916 can also operate in accordance with some FCC regulations. According to section 18.301 of the FCC regulations the ISM bands within the USA include 6.78, 13.56, 27.12, 30.68, 915, 2450, and 5800 MHz as well as 24.125, 61.25, 122.50, and 245 GHz. Globally other ISM bands, including 433 MHz, are defined by the International Telecommunications Union in some geographic locations. The list of prohibited frequency bands defined in 18.303 are "the following safety, search and rescue frequency bands is prohibited: 490-510 kHz, 2170-2194 kHz, 8354-8374 kHz, 121.4-121.6 MHz, 156.7-156.9 MHz, and 242.8-243.2 MHz." Section 18.305 stipulates the field strength and emission levels ISM equipment must not exceed when operated outside defined ISM bands. In summary, it may be concluded that ISM equipment may be operated worldwide within ISM bands as well as within most other frequency bands above 9 KHz given that the limits on field strengths and emission levels specified in section 18.305 are maintained by design or by active control. As an alternative, commercially available ISM transceivers, including commercially available integrated circuit ISM transceivers, may be designed to fulfill these field strengths and emission level requirements when used properly.

In one configuration, the telemetry transceiver 1916 can also operate in unlicensed ISM bands or in unlicensed operation of low power equipment, wherein the ISM equipment (e.g., telemetry transmitter 1916) may be operated on ANY frequency above 9 kHz except as indicated in Section 18.303 of the FCC code.

Wireless operation eliminates distortion of, or limitations on, measurements caused by the potential for physical interference by, or limitations imposed by, wiring and cables coupling the wireless sensing module or device with a power source or with data collection, storage, or display equipment. Power for the sensing components and electronic circuits is maintained within the wireless sensing module or device on an internal energy storage device. This energy storage device is charged with external power sources including, but not limited to, a battery or batteries, super capacitors, capacitors, an alternating current power supply, a radio frequency receiver, an electromagnetic induction coil, a photoelectric cell or cells, a thermocouple or thermocouples, or an ultrasound transducer or transducers. The wireless sensing module may be operated with a single charge until the internal energy source is drained or the energy source may be recharged periodically to enable continuous operation. The embedded power supply minimizes additional sources of energy radiation required to power the wireless sensing module or device during measurement operations. Telemetry functions are also integrated within the wireless sensing module or device. Once initiated the telemetry transmitter continuously broadcasts measurement data in real time. Telemetry data may be received and decoded with commercial receivers or with a simple, low cost custom receiver.

Figure 20:
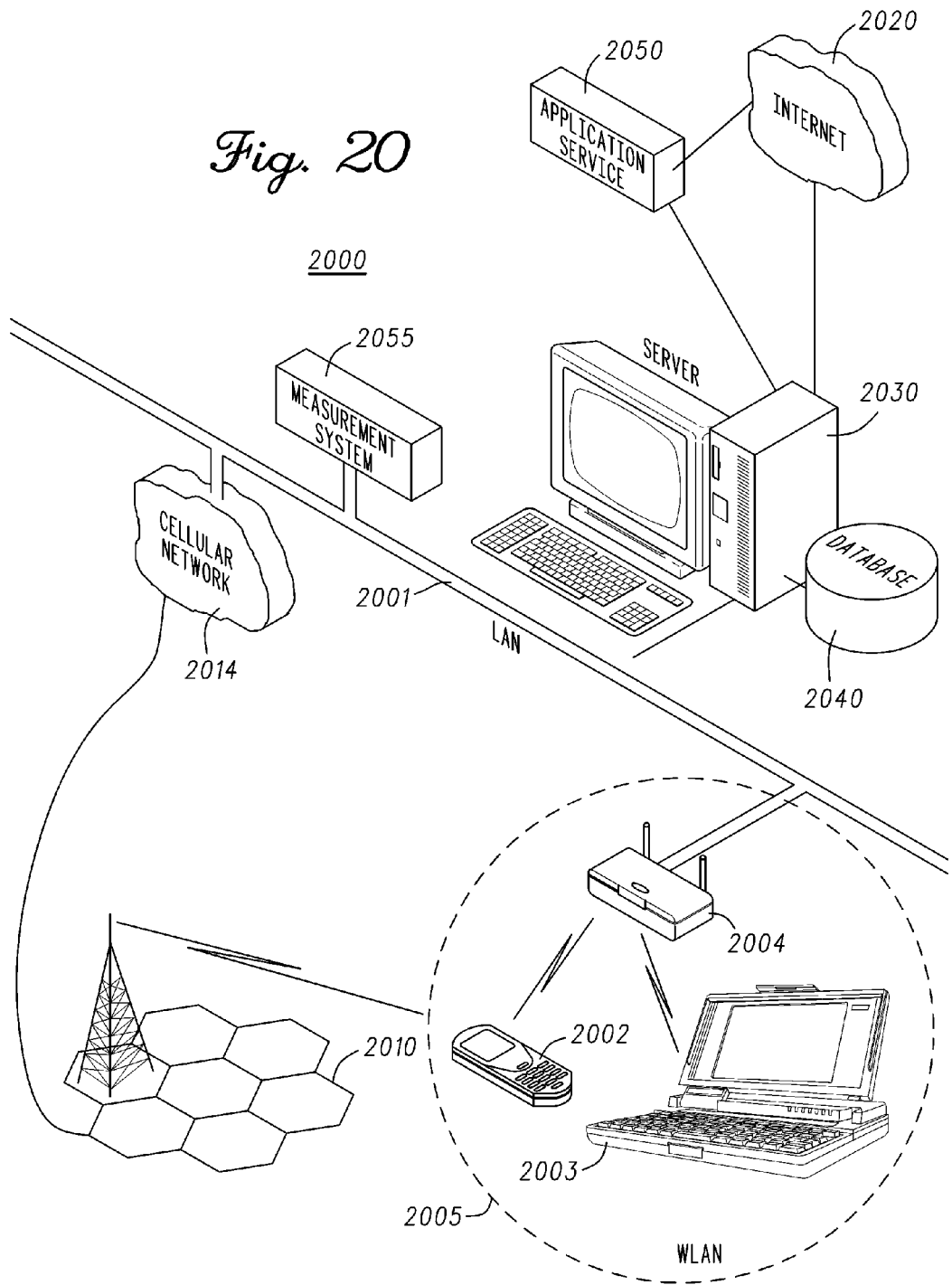
FIG. 20 illustrates a communication network for measurement and reporting in accordance with an example embodiment.

FIG. 20 illustrates a communication network 2000 for measurement and reporting in accordance with an example embodiment. Briefly, communication network 2000 expands broad data connectivity to other devices or services. As illustrated, the measurement and reporting system 2055 can be communicatively coupled to the communications network 2000 and any associated systems or services.

As one example, the measurement system 2055 can share its parameters of interest (e.g., angles, load, balance, distance, alignment, displacement, movement, rotation, and acceleration) with remote services or providers, for instance, to analyze or report on surgical status or outcome. This data can be shared for example with a service provider to monitor progress or with plan administrators for surgical monitoring purposes or efficacy studies. The communication network 2000 can further be tied to an Electronic Medical Records (EMR) system to implement health information technology practices. In other embodiments, the communication network 2000 can be communicatively coupled to HIS Hospital Information System, HIT Hospital Information Technology and HIM Hospital Information Management, EHR Electronic Health Record, CPOE Computerized Physician Order Entry, and CDSS Computerized Decision Support Systems. This provides the ability of different information technology systems and software applications to communicate, to exchange data accurately, effectively, and consistently, and to use the exchanged data.

The communications network 2000 can provide wired or wireless connectivity over a Local Area Network (LAN) 2001, a Wireless Local Area Network (WLAN) 2005, a Cellular Network 2014, and/or other radio frequency (RF) system. The LAN 2001 and WLAN 2005 can be communicatively coupled to the Internet 2020, for example, through a central office. The central office can house common network switching equipment for distributing telecommunication services. Telecommunication services can include traditional POTS (Plain Old Telephone Service) and broadband services such as cable, HDTV, DSL, VoIP (Voice over Internet Protocol), IPTV (Internet Protocol Television), Internet services, and so on.

The communication network 2000 can utilize common computing and communications technologies to support circuit-switched and/or packet-switched communications. Each of the standards for Internet 2020 and other packet switched network transmission (e.g., TCP/IP, UDP/IP, HTML, HTTP, RTP, MMS, SMS) represent examples of the state of the art. Such standards are periodically superseded by faster or more efficient equivalents having essentially the same functions. Accordingly, replacement standards and protocols having the same functions are considered equivalent.

The cellular network 2014 can support voice and data services over a number of access technologies such as GSM-GPRS, EDGE, CDMA, UMTS, WiMAX, 2G, 3G, 4G, WAP, software defined radio (SDR), and other known technologies. The cellular network 2014 can be coupled to base receiver 2010 under a frequency-reuse plan for communicating with mobile devices 2002.

The base receiver 2010, in turn, can connect the mobile device 2002 to the Internet 2020 over a packet switched link. Internet 2020 can support application services and service layers for distributing data from the measurement system 2055 to the mobile device 2002. The mobile device 2002 can also connect to other communication devices through the Internet 2020 using a wireless communication channel.

The mobile device 2002 can also connect to the Internet 2020 over the WLAN 2005. Wireless Local Access Networks (WLANs) provide wireless access within a local geographical area. WLANs are typically composed of a cluster of Access Points (APs) 2004 also known as base stations. The measurement system 2055 can communicate with other WLAN stations such as laptop 2003 within the base station area. In typical WLAN implementations, the physical layer uses a variety of technologies such as 802.11b or 802.11g WLAN technologies. The physical layer may use infrared, frequency hopping spread spectrum in the 2.4 GHz Band, direct sequence spread spectrum in the 2.4 GHz Band, or other access technologies, for example, in the 5.8 GHz ISM band or higher ISM bands (e.g., 24 GHz, etc).

By way of the communication network 2000, the measurement system 2055 can establish connections with a remote server 2030 on the network and with other mobile devices for exchanging data. The remote server 2030 can have access to a database 2040 that is stored locally or remotely and which can contain application specific data. The remote server 2030 can also host application services directly, or over the internet 2020.

It should be noted that very little data exists on implanted orthopedic devices. Most of the data is empirically obtained by analyzing orthopedic devices that have been used in a human subject or simulated use. Wear patterns, material issues, and failure mechanisms are studied. Although information can be garnered through this type of empirical study, it does not yield substantive data about the initial installation, post-operative use, and long-term use from a measurement perspective. Just as each person is different, each device installation is different having variations in initial loading, balance, and alignment. Having measured quantitative data and using the data to install an orthopedic device will greatly increase the consistency of the implant procedure thereby reducing rework and maximizing the life of the device. In at least one example embodiment, the measured data can be collected to a database where it can be stored and analyzed. For example, once a relevant sample of the measured data is collected, it can be used to define optimal initial measured settings, geometries, and alignments for maximizing the life and usability of an implanted orthopedic device.

FIG. 21 illustrates a diagrammatic representation of a machine in the form of a computer system 2100 within which a set of instructions, when executed, may cause the machine to perform any one or more of the methodologies discussed above. In some embodiments, the machine operates as a standalone device. In some embodiments, the machine may be connected (e.g., using a network) to other machines. In a networked deployment, the machine may operate in the capacity of a server or a client user machine in server-client user network environment, or as a peer machine in a peer-to-peer (or distributed) network environment.

The machine may comprise a server computer, a client user computer, a personal computer (PC), a tablet PC, a laptop computer, a desktop computer, a control system, a network router, switch or bridge, or any machine capable of executing a set of instructions (sequential or otherwise) that specify actions to be taken by that machine. It will be understood that a device of the present disclosure includes broadly any electronic device that provides voice, video or data communication. Further, while a single machine is illustrated, the term "machine" shall also be taken to include any collection of machines that individually or jointly execute a set (or multiple sets) of instructions to perform any one or more of the methodologies discussed herein.

The computer system 2100 may include a processor 2102 (e.g., a central processing unit (CPU), a graphics processing unit (GPU, or both), a main memory 2104 and a static memory 2106, which communicate with each other via a bus 2108. The computer system 2100 may further include a video display unit 2110 (e.g., a liquid crystal display (LCD), a flat panel, a solid-state display, or a cathode ray tube (CRT)). The computer system 2100 may include an input device 2112 (e.g., a keyboard), a cursor control device 2114 (e.g., a mouse), a disk drive unit 2116, a signal generation device 2118 (e.g., a speaker or remote control) and a network interface device 2120.

The disk drive unit 2116 can be other types of memory such as flash memory and may include a machine-readable medium 2122 on which is stored one or more sets of instructions (e.g., software 2124) embodying any one or more of the methodologies or functions described herein, including those methods illustrated above. The instructions 2124 may also reside, completely or at least partially, within the main memory 2104, the static memory 2106, and/or within the processor 2102 during execution thereof by the computer system 2100. The main memory 2104 and the processor 2102 also may constitute machine-readable media.

Dedicated hardware implementations including, but not limited to, application specific integrated circuits, programmable logic arrays and other hardware devices can likewise be constructed to implement the methods described herein. Applications that may include the apparatus and systems of various embodiments broadly include a variety of electronic and computer systems. Some embodiments implement functions in two or more specific interconnected hardware modules or devices with related control and data signals communicated between and through the modules, or as portions of an application-specific integrated circuit. Thus, the example system is applicable to software, firmware, and hardware implementations.

In accordance with various embodiments of the present disclosure, the methods described herein are intended for operation as software programs running on a computer processor. Furthermore, software implementations can include, but not limited to, distributed processing or component/object distributed processing, parallel processing, or virtual machine processing can also be constructed to implement the methods described herein.

The present disclosure contemplates a machine readable medium containing instructions 2124, or that which receives and executes instructions 2124 from a propagated signal so that a device connected to a network environment 2126 can send or receive voice, video or data, and to communicate over the network 2126 using the instructions 2124. The instructions 2124 may further be transmitted or received over a network 2126 via the network interface device 2120.

While the machine-readable medium 2122 is shown in an example embodiment to be a single medium, the term "machine-readable medium" should be taken to include a single medium or multiple media (e.g., a centralized or distributed database, and/or associated caches and servers) that store the one or more sets of instructions. The term "machine-readable medium" shall also be taken to include any medium that is capable of storing, encoding or carrying a set of instructions for execution by the machine and that cause the machine to perform any one or more of the methodologies of the present disclosure.

The term "machine-readable medium" shall accordingly be taken to include, but not be limited to: solid-state memories such as a memory card or other package that houses one or more read-only (non-volatile) memories, random access memories, or other re-writable (volatile) memories; magneto-optical or optical media such as a disk or tape; and carrier wave signals such as a signal embodying computer instructions in a transmission medium; and/or a digital file attachment to e-mail or other self-contained information archive or set of archives is considered a distribution medium equivalent to a tangible storage medium. Accordingly, the disclosure is considered to include any one or more of a machine-readable medium or a distribution medium, as listed herein and including art-recognized equivalents and successor media, in which the software implementations herein are stored.

Although the present specification describes components and functions implemented in the embodiments with reference to particular standards and protocols, the disclosure is not limited to such standards and protocols. Each of the standards for Internet and other packet switched network transmission (e.g., TCP/IP, UDP/IP, HTML, HTTP) represent examples of the state of the art. Such standards are periodically superseded by faster or more efficient equivalents having essentially the same functions. Accordingly, replacement standards and protocols having the same functions are considered equivalents.

The illustrations of embodiments described herein are intended to provide a general understanding of the structure of various embodiments, and they are not intended to serve as a complete description of all the elements and features of apparatus and systems that might make use of the structures described herein. Many other embodiments will be apparent to those of skill in the art upon reviewing the above description. Other embodiments may be utilized and derived therefrom, such that structural and logical substitutions and changes may be made without departing from the scope of this disclosure. Figures are also merely representational and may not be drawn to scale. Certain proportions thereof may be exaggerated, while others may be minimized. Accordingly, the specification and drawings are to be regarded in an illustrative rather than a restrictive sense.

In general, artificial components for other joint replacement surgeries have a similar operational form as the knee joint example. The joint typically comprises two or more bones with a cartilaginous surface as an articular surface that allows joint movement. The cartilage also acts to absorb loading on the joint and prevents bone-to-bone contact. Reconstruction of the hip, spine, shoulder, and other joints has similar functioning insert structures having at least one articular surface. Like the knee joint, these other insert structures typically comprise a polymer material. The polymer material is formed for a particular joint structure. For example, the hip insert is formed in a cup shape that is fitted into the pelvis. In general, the size and thickness of these other joint inserts allow the integration of the sensing module. It should be noted that the sensing module disclosed herein contemplates use in both trial inserts and permanent inserts for the other joints of the muscular-skeletal system thereby providing quantitative parameter measurements during and post surgery.

While the present invention has been described with reference to particular embodiments, those skilled in the art will recognize that many changes may be made thereto without departing from the spirit and scope of the present invention. Each of these embodiments and obvious variations thereof is contemplated as falling within the spirit and scope of the invention.

What is claimed is:

1. An insert comprising:
   a flexible articular surface, where the flexible articular surface is an outer surface of a first component;
   a rigid load plate where the rigid load plate includes at least one opening;
   a first sensor coupled to a first load pad, where the first load pad has an area greater than or equal to a first area of the first sensor;
   a second sensor coupled to a second load pad, where the second load pad has an area greater than or equal to a second area of the second sensor;
   a third sensor coupled to a third load pad, where the third load pad has an area greater than or equal to a third area of the third sensor; and
   a second component, where the load plate is configured to transmit a portion of a load on the load surface to the first, second and third sensors, where the load plate lies between the first and second component, where the first, second, and third sensors lie between the first and second components, where at least one alignment feature extends from the second component through the rigid load plate and couples to the first component and where the portion of the load exerts a force on the first, second, and third sensors and the first, second and third load pads.

2. The insert of claim 1 where the insert is hermetically sealed from an external environment.

3. The insert of claim 2 where the insert is sealed prior to a sterilization process.

4. The insert of claim 3 where the flexible load surface includes an articular surface.

5. The insert of claim 4 where an adhesive couples the first component and second component together such that liquids, solids, and gases cannot enter or leave the cavity.

6. The insert of claim 4 where the first and second components are welded together such that liquids, solids, and gases cannot enter or leave the cavity.

7. The insert of claim 4 where the first and second components are mechanically coupled together such that liquids, solids, and gases cannot enter or leave the cavity.

8. The insert of claim 3 where the insert includes a transmitter.

9. The insert of claim 8 where the transmitter is configured to transmit data from at least one of the first, second and third sensors.

10. The insert of claim 1 further including electronic circuitry operatively coupled to the first, second, and third sensors within a cavity wherein the electronic circuitry underlies the rigid load plate.

11. The insert of claim 10 further including a power source coupled to the electronic circuitry in the cavity.

12. The insert of claim 1 where the insert comprises polycarbonate.

13. An insert measurement system for measuring loading applied by the muscular-skeletal system comprising:
   a first component, where the first component includes a flexible articular surface;
   a second component, where the second component is configured to form a cavity when attached to the first component;
   a rigid load plate, where the first component is configured to transfer a portion of a load on the articular surface to the load plate, where the load plate is configured to fit within the cavity and where the rigid load plate includes at least one opening;
   a plurality of sensors configured to fit within the cavity, where each sensor of the plurality of sensors is configured to couple to a corresponding load pad, where the rigid load plate is configured to transmit the portion of the load on the articular surface to the plurality of sensors, and where at least one alignment feature extends from the second component through the rigid load plate and couples to the first component.

14. The insert measurement system of claim 13 where first and second components each have a peripheral surface, where the peripheral surfaces are coupled together to seal the cavity, and where the seal is hermetic.

15. The insert measurement system of claim 14 where an adhesive is used to attach and seal the peripheral surfaces of the first and second components.

16. The insert measurement system of claim 15 further including electronic circuitry operatively coupled to the plurality of sensors wherein the electronic circuitry underlies the rigid load plate in the cavity.

* * * * *